US011634465B2

(12) United States Patent
Shoshan-Barmatz

(10) Patent No.: US 11,634,465 B2
(45) Date of Patent: Apr. 25, 2023

(54) ANALOGUES OF VDAC1-DERIVED PEPTIDES

(71) Applicants: B. G. NEGEV TECHNOLOGIES AND APPLICATIONS LTD., AT BEN-GURION UNIVERSITY, Beer Sheva (IL); THE NATIONAL INSTITUTE FOR BIOTECHNOLOGY IN THE NEGEV LTD., Beer Sheva (IL)

(72) Inventor: Varda Shoshan-Barmatz, Omer (IL)

(73) Assignees: B. G. NEGEV TECHNOLOGIES AND APPLICATIONS LTD., AT BEN-GURION UNLVERSITY, Beer Sheva (IL); THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 35 days.

(21) Appl. No.: 17/039,042

(22) Filed: Sep. 30, 2020

(65) Prior Publication Data

US 2021/0079052 A1  Mar. 18, 2021

Related U.S. Application Data

(60) Division of application No. 16/451,520, filed on Jun. 25, 2019, now Pat. No. 10,829,530, which is a division of application No. 15/868,252, filed on Jan. 11, 2018, now Pat. No. 10,385,104, which is a continuation of application No. PCT/IL2016/050958, filed on Sep. 1, 2016.

(60) Provisional application No. 62/213,667, filed on Sep. 3, 2015.

(51) Int. Cl.

| C07K 14/47 | (2006.01) |
|---|---|
| C07K 14/79 | (2006.01) |
| A61P 1/16 | (2006.01) |
| A61P 35/02 | (2006.01) |
| A61P 35/00 | (2006.01) |
| A61K 38/00 | (2006.01) |

(52) U.S. Cl.
CPC ............ C07K 14/4747 (2013.01); A61P 1/16 (2018.01); A61P 35/00 (2018.01); A61P 35/02 (2018.01); C07K 14/79 (2013.01); A61K 38/00 (2013.01); C07K 2319/00 (2013.01); C07K 2319/10 (2013.01)

(58) Field of Classification Search
CPC . A61K 38/00; A61P 1/16; A61P 35/00; A61P 35/02; C07K 14/4747; C07K 14/79; C07K 2319/00; C07K 2319/10
See application file for complete search history.

(56) References Cited

U.S. PATENT DOCUMENTS

| 5,780,235 A | 7/1998 | Bandman |
|---|---|---|
| 8,119,601 B2 | 2/2012 | Shoshan-Barmatz |
| 8,648,045 B2 | 2/2014 | Shoshan-Barmatz |
| 2012/0214741 A1 | 8/2012 | Shoshan-Barmatz |

FOREIGN PATENT DOCUMENTS

| JP | 2010-526099 A | 7/2010 |
|---|---|---|
| JP | 2014-528700 A | 10/2014 |
| WO | 2006095347 A2 | 9/2006 |
| WO | 2015011711 A1 | 1/2015 |

OTHER PUBLICATIONS

Varda Shoshan-Barmatz, VDAC1, mitochondrial dysfunction, and Alzheimer's disease, Pharmacological Research 131 (2018) 87-101.*
Andrieu et al., (1989) Pharmacokinetic evaluation of indomethacin nanocapsules. Drug Des Deliv 4(4): 295-302.
Bakiri and Wagner (2013) Mouse models for liver cancer. Mol Oncol 7(2): 206-223.
Bien-Ly et al., (2014) Transferrin receptor (TfR) trafficking determines brain uptake of TfR antibody affinity variants. J Exp Med 211(2): 233-244.
Blachly-Dyson et al., (1993) Cloning and functional expression in yeast of two human isoforms of the outer mitochondrial membrane channel, the voltage-dependent anion channel. J Biol Chem 268(3): 1835-1841.
Czaja (2014) Hepatic inflammation and progressive liver fibrosis in chronic liver disease. World J Gastroenterol 20(10): 2515-2532.
Das et al., (2014) Assessment of drug delivery and anticancer potentials of nanoparticles-loaded siRNA targeting STAT3 in lung cancer, in vitro and in vivo. Toxicol Lett 225(3): 454-466.
De Pinto et al., (2010) Characterization of human VDAC isoforms: a peculiar function for VDAC3? Biochim Biophys Acta 1797(6-7): 1268-1275.
Fujii et al., (2013) A murine model for non-alcoholic steatohepatitis showing evidence of association between diabetes and hepatocellular carcinoma. Med Mol Morphol 46(3): 141-152.
Guichard et al., (1994) Antigenic mimicry of natural L-peptides with retro-inverso-peptidomimetics. Proc Natl Acad Sci U S A 91(21): 9765-9769.
Kleiner et al., (2005) Design and validation of a histological scoring system for nonalcoholic fatty liver disease. Hepatology 41(6): 1313-1321.
Krasnov et al., (2013) Targeting VDAC-bound hexokinase II: a promising approach for concomitant anti-cancer therapy. Expert Opin Ther Targets 17(10): 1221-1233.

(Continued)

*Primary Examiner* — Julie Ha
*Assistant Examiner* — Erinne R Dabkowski
(74) *Attorney, Agent, or Firm* — Browdy and Neimark, PLLC

(57) ABSTRACT

The present invention relates to peptides comprising analogues of VDAC1-derived peptides having improved pharmacokinetic characteristics compared to the native parent peptides, which are effective in impairing cell energy production, in inducing apoptosis and cell death, particularly of cancerous cells, in eliminating cancer stem cells and in reducing symptoms associated with fat accumulation in liver cells particularly with nonalcoholic fatty liver disease (NAFLD) and symptoms associated thereto.

9 Claims, 32 Drawing Sheets

Specification includes a Sequence Listing.

(56) References Cited

OTHER PUBLICATIONS

Lee et al., (2001) Receptor mediated uptake of peptides that bind the human transferrin receptor. Eur J Biochem 268(7): 2004-2012.

Lemasters and Holmuhamedov (2006) Voltage-dependent anion channel (VDAC) as mitochondrial governator—thinking outside the box. Biochim Biophys Acta 1762(2): 181-190.

Liangpunsakul and Chalasani (2003) Treatment of Nonalcoholic Fatty Liver Disease. Curr Treat Options Gastroenterol 6(6): 455-463.

Martinello et al., (2015) Might the Masson trichrome stain be considered a useful method for categorizing experimental tendon lesions? Histol Histopathol 30(8): 963-969.

Pierce and Keating (2014) Creating anatomically accurate and reproducible intracranial xenografts of human brain tumors. J Vis Exp (91): 52017; 8 pages.

Pittala et al., "Evaluating Efficacy of VDAC1-Based Peptides Treatment in DEN-Induced Liver Cancer Model". Presented in the 2016 International Pelviperineology Conference held in Tel Aviv—Yafo, Israel Sep. 21-24, 2016; 1 page.

Pollard et al., (2009) Glioma stem cell lines expanded in adherent culture have tumor-specific phenotypes and are suitable for chemical and genetic screens. Cell Stem Cell 4(6): 568-580.

Prezma et al., (2013) VDAC1-based peptides: novel pro-apoptotic agents and potential therapeutics for B-cell chronic lymphocytic leukemia. Cell Death Dis 4: e809; 11 pages.

Scorletti et al., (2014) Effects of purified eicosapentaenoic and docosahexaenoic acids in nonalcoholic fatty liver disease: results from the Welcome* study. Hepatology 60(4): 1211-1221.

Shirakami et al., (2012) Diethylnitrosamine-induced hepatocarcinogenesis is suppressed in lecithin:retinol acyltransferase-deficient mice primarily through retinoid actions immediately after carcinogen administration. Carcinogenesis 33(2): 268-274.

Shoshan-Barmatz and Ben-Hail (2012) VDAC, a multi-functional mitochondrial protein as a pharmacological target. Mitochondrion 12(1): 24-34.

Shoshan-Barmatz and Golan (2012) Mitochondrial VDAC1: function in cell life and death and a target for cancer therapy. Curr Med Chem 19(5): 714-735.

Shoshan-Barmatz et al., (2010) VDAC, a multi-functional mitochondrial protein regulating cell life and death. Mol Aspects Med 31(3): 227-285.

Shoshan-Barmatz et al., (2015) The mitochondrial voltage-dependent anion channel 1 in tumor cells. Biochim Biophys Acta 1848(10 Pt B): 2547-2575.

Shteinfer-Kuzmine et al., (2017) Mitochondrial VDAC1-based peptides: Attacking oncogenic properties in glioblastoma. Oncotarget 8(19): 31329-31346.

Shteinfer-Kuzmine et al., (2018) Selective induction of cancer cell death by VDAC1-based peptides and their potential use in cancer therapy. Mol Oncol 12(7): 1077-1103.

Tempel-Brami et al., (2015) Practical Applications of in Vivo and ex Vivo MRI in Toxicologic Pathology Using a Nove High-performance Compact MRI System. Toxicol Pathol 43(5): 633-650.

Tolba et al., (2015) Diethylnitrosamine (DEN)-induced carcinogenic liver injury in mice. Lab Anim 49(1 Suppl): 59-69.

Tugyi et al., (2005) Partial D-amino acid substitution: Improved enzymatic stability and preserved Ab recognition of a MUC2 epitope peptide. Proc Natl Acad Sci U S A 102(2): 413-418.

Yip et al., (2006) Alcoholic liver disease. Semin Diagn Pathol 23(3-4): 149-160.

Zhang et al., (2014) E2F1 is a novel fibrogenic gene that regulates cholestatic liver fibrosis through the Egr-1/SHP/EID1 network. Hepatology 60(3): 919-930.

Lifetein, published online May 12, 2012, https://www.lifetein.com/Peptide-Synthesis-D-Amino-Acid.html; 5 pages.

Mechanisms of Carcinogenesis, section 3, 2008, International Agency for Research on Cancer.

Retro Inverse Peptides (online), published online: Jun. 4, 2014 (retrieved from the internet on Jun. 12, 2016) Retrieved from the internet: <URL: http://www.biosyn.com/tew/retro-inverso-peptides.aspx>. Apr. 6, 2014 (Apr. 6, 2014); 1 page.

Chen et al., (2013) Retro-inverso carbohydrate mimetic peptides with annexin1-binding selectivity, are stable in vivo, and target tumor vasculature. PLoS One 8(12): e80390.

* cited by examiner

Ballooning

Inflammation

ANALOGUES OF VDAC1-DERIVED PEPTIDES

The Sequence Listing in ASCII text file format of 6,527 bytes in size, created on Sep. 28, 2020, with the file name "2020-09-30SequenceListing_Shoshan8B," filed in the U.S. Patent and Trademark Office on even date herewith, is hereby incorporated herein by reference.

FIELD OF THE INVENTION

The present invention relates to peptides comprising analogues of VDAC1-derived peptides having improved pharmacokinetic characteristics compared to the native parent peptides, which are effective in impairing cell energy production, in inducing apoptotic cell death, particularly of cancerous cells, in eliminating cancer stem cells and in reducing symptoms associated with steatosis, inflammation and fibrosis in liver cells associated with nonalcoholic fatty liver disease (NAFLD).

BACKGROUND OF THE INVENTION

Voltage-dependent anion channel (VDAC; mitochondrial porin) is found in the outer mitochondrial membrane in all eukaryotic cells. VDAC is a central player in cell energy metabolism and have a key role in mitochondria-mediated apoptosis, and controls the fluxes of ions and metabolites between the mitochondrion and the cytosol. VDAC also provides a point of convergence for a variety of cell survival and death signals, mediated via its association with various ligands and proteins. VDAC is a key player in mitochondria-mediated apoptosis, participating in the release of mitochondria pro-apoptotic proteins (e.g. cytochrome c, apoptosis inducing factor (AIF) and second mitochondria-derived activator of caspases (Smac/DIABLO)) to the cytosol and interacts with apoptosis regulatory proteins such as Bcl-2, Bcl-xL and hexokinase (HK).

Three mammalian isoforms of VDAC are known, VDAC1, VDAC2 and VDAC3, where VDAC1 is the major isoform expressed in mammalian cells (De Pinto, V., et. al. 2010. Biochim Biophys Acta 1797:1268-1275). Blachly-Dysion et al. (Blachly-Dyson E et al., 1993. J Biol Chem. 268(3):1835-41) disclosed the cloning and functional expression in yeast of two human VDAC isoforms, VDAC1 and VDAC2. U.S. Pat. No. 5,780,235 discloses two VDAC sequences, which were named HACH (Human Voltage-Dependent Anion Channel), subsequently identified as VDAC2 and VDAC3. That patent provides genetically engineered expression vectors, host cells containing the vector, a method for producing HACH and a method for identifying pharmaceutical compositions inhibiting the expression and activity of HACH as well as the use of such compositions for the treatment of cancer and proliferative diseases.

Apoptosis, also known as programmed cell death, plays a central role in, inter alia, development, immune cell regulation and tissue homeostasis in multicellular organisms. Genetic and molecular analysis from various species has indicated that the apoptotic pathway is highly conserved. In addition to being essential for normal development and maintenance, apoptosis is important in the defense against viral infection and in preventing cancer. Mitochondria play an important role in apoptotic cell death. The release of apoptogenic proteins such as cytochrome c from the mitochondrion intermembranal space into the cytoplasm of the cell initiates a cascade of steps involved in caspase activation that executes the cell death program. Substantial evidence links VDAC1 to apoptosis and suggests that VDAC1 is a critical player in the release of apoptogenic proteins from mitochondria in mammalian cells (Lemasters, J. J., and Holmuhamedov, E. 2006. Biochim. Biophys Acta 1762:181-190; Shoshan-Barmatz V et al. 2010. Molecular Aspects of Medicine 31(3):227-286; Shoshan-Barmatz V and Ben-Hail D. 2012. Mitochondrion 12(1):24-34; Shoshan-Barmatz V and Golan M. 2012. Current Medicinal Chemistry 19(5): 714-35; Shoshan-Barmatz, V et al. 2015. Biochim Biophys Acta, 1848(10 Pt B):2547-75).

It has been previously shown that peptides derived from VDAC are capable of inducing apoptosis (Prezma T et al. 2013. Cell Death and Disease 4:e809).

U.S. Pat. Nos. 8,119,601 and 8,648,045 to the inventor of the present invention and others disclose isolated VDAC1 derived peptides that are capable of inducing apoptosis in a cell and to pharmaceutical compositions comprising same useful in the treatment of disease associated with aberrant apoptosis, particularly cancer. The peptides are derived from the N-terminal domain of VDAC1 as well as from VDAC1 β-strand 14 and its cytosolic β-loop.

International Patent Application Publication No. WO 2015/011711 the inventor of the present invention and others discloses short peptides based on the amino acids sequence of the N-terminal domain of the human mitochondrial protein voltage-dependent anion channel 1 (VDAC) and to peptide conjugates further comprising a cell permeability enhancing moiety. The peptides, peptide conjugates and pharmaceutical composition comprising same are useful for treating diseases characterized by cell hyper-proliferation or resistance to cell death, particularly cancer.

Prezma et al. (Prezma T et al., 2013. Cell Death Dis. 19(4):e809) showed that VDAC1-based peptides, including short peptides, selectively induced cells death of peripheral mononuclear cells (PBMC) from patients with B-chronic lymphocytic leukemia (CLL) while exhibiting minor effects on PBMCs from healthy donor.

Non-alcoholic fatty liver disease (NAFLD) is often "silent" liver disease and characterized by an excessive abnormal accumulation of fatty acids and triglycerides within the cytoplasm of the hepatocytes and other liver cells of non-alcohol users. NAFLD has emerged as a significant public health concerns in Western societies and is the most common cause of abnormal liver function. NAFLD is a continuum chronic fatty liver diseases ranging from benign hepatic steatosis and its progressive form called non-alcoholic steatohepatitis (NASH). In NASH, fat accumulation in the liver is associated with inflammation and different degrees of scarring. NASH is a potentially serious condition that carries a substantial risk of progression to end-stage liver disease, cirrhosis and hepatocellular carcinoma (HCC). Some patients who develop cirrhosis are at risk of liver failure and may eventually require a liver transplant.

Nonalcoholic fatty liver disease is classified as isolated fatty liver (IFL) and NASH. In both IFL and NASH there is an abnormal amount of fat in the liver cells, but, in addition, in NASH there is inflammation within the liver, and, as a result, the liver cells are damaged, and when die, they are replaced by scar tissue leading to cirrhosis.

The cause NAFLDs is complex and not completely understood. With that, NAFLD is universally considered as the hepatic manifestation of the metabolic syndrome (MS) and insulin resistance is regarded as its key pathophysiological hallmark. Given the strong association of NAFLD with metabolic syndrome as well as the worldwide epidemic of obesity, the prevalence of NAFLD and NASH are increasing. NAFLD is more prevalent in cohorts of patients with pre-existing metabolic conditions than the general population. Specifically, type II diabetes mellitus and NAFLD have a particularly close relationship. A study of patients with type II diabetes mellitus reported a 69% prevalence of ultrasonographic NAFLD. However, no relationship was evident between diabetic degenerative complications or glycaemic control and the presence of NAFLD. The prevalence of simple steatosis in obese individuals ranges from 30% to 37%, while in NAFLD ranges from 57% of overweight individuals attending out-patient clinics to 98% of nondiabetic obese patients.

There are no drugs currently approved to prevent or treat NAFLD or NASH and thus current therapies rely on lifestyle modifications and treatments with disease associated with NAFLD. The most important recommendations given to persons with this disease include reducing weight (if obese or overweight), following a balanced and healthy diet, increasing physical activity, avoiding alcohol and unnecessary medications, and in some cases bariatric surgery, where the main goal is to reduce disease symptoms after diagnosis.

Mitochondria can influence cell fate at the levels of energy production, lipid metabolism, production, and detoxification of reactive oxygen species (ROS) and release of pro-apoptotic proteins. Various studies showed that mitochondria harbor prominent morphologic role of these organelles in the pathogenesis of hepatosteatosis.

A major obstacle to the in vivo therapeutic use of peptides is their susceptibility to proteolytic degradation. Retro-inverso peptides are peptides whose amino acid sequence is reversed and the α-center chirality of the amino acid subunits is inverted as well. Usually, these types of peptides are designed by including D-amino acids in the reverse sequence to help maintain side chain topology similar to that of the original L-amino acid peptide and make them more resistant to proteolytic degradation. Other reported synonyms for these peptides in the scientific literature include All-D-Retro Peptides, Retro-Enantio Peptides, Retro-Inverso Analogs, Retro-Inverso Analogues, Retro-Inverso Derivatives, Retro-Inverso peptides and Retro-Inverso Isomers. D-amino acids represent conformational mirror images of natural L-amino acids occurring in natural proteins present in biological systems. There are also partially modified retro-inverso analogues of linear peptides in which only some of the peptide bonds are reversed and the chirality of the amino acid residues in the reversed portion is inverted.

Peptides that contain D-amino acids are typically less susceptible to proteolytic degradation and have a longer effective time when used as pharmaceuticals. If properly designed, retro-inverso peptides can have binding characteristics similar to L-peptides. Retro-inverso peptides are useful candidates for the study of protein-protein interactions by designing peptidomimetics that mimic the shape of peptide epitopes, protein-protein, or protein-peptide interfaces. Retro-inverso-peptides are attractive alternatives to L-peptides used as pharmaceuticals. These peptides have been reported to elicit lower immunogenic responses compared to L-peptides. However, although retro-inverso analogues exhibit increased metabolic stability, their biological activity is often greatly compromised (Guichard G et al., 1994. Proc. Natl. Acad. Sci. U.S.A., 91:9765-9769).

There is an unmet need for and it would be highly advantageous to have VDAC1-based peptides exhibiting improved pharmacokinetic characteristics while at least retaining their biological activity.

SUMMARY OF THE INVENTION

The present invention answers the above-mentioned need by providing analogues of VDAC1-based peptides with superior pharmacokinetic characteristics. The present invention provides synthetic peptides comprising analogues of VDAC1-derived peptides, particularly to retro- and partially or fully inverso analogues, wherein the VDAC1-derived peptides forming the basis for the analogues of the present invention have been shown to induce apoptosis in cancerous cells. The analogues of the present invention were found to have improved solubility in pharmaceutically compatible solvents and improved stability compared to the previously disclosed native peptides, while at least keeping the activity of the native proteins, altogether making them better candidates as therapeutic agents for the treatment of diseases characterized by cell hyper-proliferation or by resistance to cell death, particularly for treating cancer. Unexpectedly, the analogues of VDAC1-derived peptides were shown to cross the blood brain barrier (BBB.) The synthetic peptides of the invention are also effective in treating cancer by eliminating cancer stem cells. Unexpectedly, the peptides of the invention are also effective in suppressing non-alcoholic steatosis and steohepatitis (NASH) pathologies. The present invention is based in part on the unexpected discovery that a peptide composed of retro-inverso analogue of a peptide derived from VDAC1 beta strand 14 and its cytosolic β-loop flanked by a tryptophan zipper and a retro analogue of transferrin receptor binding domain has increased solubility in aqueous solution, including physiological solutions, increased stability and increased cell death induction activity compared to a corresponding peptide comprising the same components in their native form. The retro-inverso analogue was found to be highly efficient in inducing death of cancerous cells, and to be able to cross the BBB. Furthermore, the retro-inverso analogue was found to be highly effective in reducing symptoms associated with fatty liver.

According to one aspect, the present invention provides a synthetic peptide comprising an analogue of VDAC1-derived peptide, the VDAC1-derived peptide is capable of inducing apoptosis in cancerous cells and consists of 5-26 contiguous amino acids, wherein the analogue is retro modified and partially or completely inverso modified with respect to said VDAC1-derived peptide.

As used herein, the term "retro modified" refers to a peptide analogue which is made up of L-amino acids in which the amino acid residues are assembled in opposite direction in respect to the peptide from which it is retro modified.

As used herein, the term "inverso modified" refers to a peptide analogue which is made up of D-amino acids in which the amino acid residues are assembled in the same direction in respect to the peptide from which it is inverso modified. A partially inverso modified analogue refers to a peptide comprising at least one D-amino acid. A completely inverso modified analogue refers to a peptide made up of D-amino acids.

According to certain embodiments, the analogue is partially inverso modified.

According to certain exemplary embodiments, the analogue is completely inverso modified.

According to certain embodiments, the VDAC1-derived peptide capable of inducing apoptosis in cancerous cell is designated LP4 and consists of the amino acid sequence set forth in SEQ ID NO:1 (KKLETAVNLAWTAGNSN). According to these embodiments, the amino acids sequence of the retro analogue is as set forth in SEQ ID NO:2 (NSNGATWALNVATELKK).

As used herein, the term "retro-inverso" analogue refers to a peptide analogue which is made up of D-amino acids in which the amino acid residues are assembled in the opposite direction with respect to the peptide from which it is retro-inverso modified.

According to certain exemplary embodiments, all the amino acids of the retro analogue as set forth in SEQ ID NO:2 are in D configuration forming a retro-inverso modified analogue of SEQ ID NO:1 having the sequence D-Asn-D-Ser-D-Asn-D-Gly-D-Ala-D-Thr-D-Trp-D-Ala-D-Leu-D-Asn-D-Val-D-Ala-D-Thr-D-Glu-D-Leu-D-Lys-D-Lys (SEQ ID NO:3).

According to certain embodiments, the VDAC1-derived peptide capable of inducing apoptosis in cancerous cells consists of the amino acid sequence set forth in SEQ ID NO:4 (MAVPPTYADLGKSARDVFTKGYGFGL), corresponding to the amino acids 1-26 at the N-terminal of the native VDAC1. According to these embodiments, the amino acids sequence of the retro analogue is as set forth in SEQ ID NO:5 (LGFGYGKTFVDRASKGLDAYTPPVAM).

According to certain exemplary embodiments, all the amino acids of the retro analogue as set forth in SEQ ID NO:5 are in D configuration forming a retro-inverso modified analogue of SEQ ID NO:4 having the sequence D-Leu-D-Gly-D-Phe-D-Gly-D-Tyr-D-Gly-D-Lys-D-Thr-D-Phe-D-Val-D-Asp-D-Arg-D-Ala-D-Ser-D-Lys-D-Gly-D-Leu-D-Asp-D-Ala-D-Tyr-D-Thr-D-Pro-D-Pro-D-Val-D-Ala-D-Met (SEQ ID NO:6).

According to certain embodiments, the synthetic peptide further comprises a cell recognition and/or localization moiety. The localization moiety typically enhances the permeability of the synthetic peptide through the cell membranes. Any recognition and/or localization moiety as is known in the art can be used according to the teachings of the present invention, and it can be connected to any position of the analogue of VDAC1-derived peptide via a direct bond or via a spacer or linker. According to certain exemplary embodiments, the cell recognition and/or localization moiety is a peptide. According to some embodiments, the localization moiety is an intra-cellular localization peptide, also referred to as cell penetrating peptide (CPP).

According to some embodiments, the recognition and/or localization peptide is all L-stereomeric peptide. According to other embodiments, the recognition and/or localization peptide is all D-stereomeric peptide.

According to some embodiments, the recognition and/or localization peptide comprises transferrin-receptor binding domain (Tf) or a fragment thereof. According to certain exemplary embodiments, the transferrin-receptor binding domain comprises the amino acid sequence set forth in SEQ ID NO:7 (HAIYPRH). According to some embodiments, the Tf peptide consists of the amino acid sequence set forth in SEQ ID NO:7. According to certain exemplary embodiments, the recognition and/or localization peptide is a retro modified analogue of SEQ ID NO:7, having the amino acid sequence set forth in SEQ ID NO:8 (HRPYIAH). According to yet additional exemplary embodiments, the transferrin-receptor binding domain comprising the amino acids sequence set forth in any one of SEQ ID NO: 7 and SEQ ID NO:8 is all L-stereomeric peptide.

According to other embodiments, the recognition and/or localization peptide is partially or completely inverso modified. According to some embodiments, the recognition and/or localization peptide is a completely inverso analogue of SEQ ID NO:7. According to certain exemplary embodiments, the recognition and/or localization peptide is a completely inverso modified analogue of SEQ ID NO:8.

According to additional certain embodiments, the recognition and/or localization peptide is an amino acid sequence comprising the Drosophila antennapedia (Antp) domain or a fragment thereof. According to some embodiments, the Antp domain comprises the amino acid sequence set forth in SEQ ID NO:9 (RQIKIWFQNRRMKWKK) or a fragment thereof. According to other embodiments, the Antp domain consists of SEQ ID NO:9.

According to other embodiments, the recognition and/or localization peptide is a partially inverso modified analogue of SEQ ID NO:9 or of a part thereof. According to additional embodiments, the recognition and/or localization peptide is a completely inverso modified analogue of SEQ ID NO:9 or of a part thereof. According to further embodiments, the recognition and/or localization peptide is a retro modified analogue of SEQ ID NO:9, having the amino acid sequence set forth in SEQ ID NO:10 (KKWKMRRNQFWIKIQR) or a part thereof. According to yet additional embodiments, the recognition and/or localization peptide is an inverso analogue of SEQ ID NO:10.

According to some embodiments, the recognition and/or localization peptide is connected to the N-terminus of the analogue of VDAC1-derived peptide, directly or indirectly. Each possibility represents a separate embodiment of the present invention.

According to certain exemplary embodiments, the recognition and/or localization peptide is connected to the C-terminus of the analogue of VDAC1-derived peptide, directly or indirectly. Each possibility represents a separate embodiment of the present invention.

Most small peptides are flexible in solution and do not adopt the structure that the same sequence adopts in the native protein. Some of the VDAC1-derived peptides, according to VDAC1 topological model, exist in the form of β-loops. Therefore, according to certain embodiments the synthetic peptides of the invention comprises the amino acids sequences SWTWE (SEQ ID NO:11) and KWTWK (SEQ ID NO:12), together the "Tryptophan (Trp) zipper peptide", each independently located at the C- or N-terminus of the analogue of the VDAC1 derived peptide. According to some embodiments, the Trp zipper peptide comprises a retro analogue of SEQ ID NO:11, said retro analogue has the amino acid sequence set forth in SEQ ID NO:13 (EWTWS). According to yet additional embodiments, the Trp zipper peptide comprises partially or completely an inverso peptide of any one of SEQ ID NOs:11-13. The Trp zipper peptide sequence can induce the formation of stable β-hairpins by tryptophan-tryptophan cross-strand pairs.

According to certain exemplary embodiments, the synthetic peptide of the invention comprises an analogue of VDAC1-derived peptide capable of inducing apoptosis and consisting of 5-26 contiguous amino acids, wherein the analogue is retro modified and partially or completely inverso modified with respect to the VDAC1-derived peptide and wherein said analogue is flanked by Trp zipper amino acids at its N- and C-terminus.

According to certain exemplary embodiments, the present invention provides a synthetic peptide comprising a retro-inverso analogue of SEQ ID NO:1 flanked by Trp zipper having the amino acids sequence set forth in SEQ ID NO:12 at its N-terminus and the amino acids sequence set forth in SEQ ID NO:13 at its C-terminus further comprising a retro analogue of a recognition and/or localization peptide, having the amino acids sequence set forth in SEQ ID NO:7. According to certain currently preferred exemplary embodiments, the synthetic peptide comprises the amino acids sequence set forth in SEQ ID NO:14 (D-Lys-D-Trp-D-Thr-D-Trp-D-Lys-D-Asn-D-Ser-D-Asn-D-Gly-D-Ala-D-Thr-D-

Trp-D-Ala-D-Leu-D-Asn-D-Val-D-Ala-D-Thr-D-Glu-D-Leu-D-Lys-D-Lys-D-Glu-D-Trp-D-Thr-D-Trp-D-ser-His-Arg-Pro-Tyr-Ile-Ala-His.

According to some embodiments, the peptide consists of the amino acids sequence set forth in SEQ ID NO:14.

According to yet additional embodiments, the present invention provides a synthetic peptide comprising a retro-inverso analogue of SEQ ID NO:4 flanked by a retro analogue of a recognition and/or localization peptide having the amino acids sequence set forth in SEQ ID NO:9 at its N-terminus. According to certain embodiments, the synthetic peptide comprises the amino acids sequence set forth in SEQ ID NO:15 (Lys-Lys-Trp-Lys-Met-Arg-Arg-Asn-Gln-Phe-Trp-Ile-Lys-Ile-Gln-Arg-D-Leu-D-Gly-D-Phe-D-Gly-D-Tyr-D-Gly-D-Lys-D-Thr-D-Phe-D-Val-D-Asp-D-Arg-D-Ala-D-Ser-D-Lys-D-Gly-D-Leu-D-Asp-D-Ala-D-Tyr-D-Thr-D-Pro-D-Pro-D-Val-D-Ala-D-Met).

According to some embodiments, the present invention provides a synthetic peptide comprising a retro-inverso analogue of SEQ ID NO:4 flanked by a recognition and/or localization peptide having the amino acids sequence set forth in SEQ ID NO:9 at its N-terminus. According to these embodiments, the synthetic peptide comprises the amino acid sequence set forth in SEQ ID NO:16 (Arg-Gln-Ile-Lys-Ile-Trp-Phe-Gln-Asn-Arg-Arg-Met-Lys-Trp-Lys-Lys-D-Leu-D-Gly-D-Phe-D-Gly-D-Tyr-D-Gly-D-Lys-D-Thr-D-Phe-D-Val-D-Asp-D-Arg-D-Ala-D-Ser-D-Lys-D-Gly-D-Leu-D-Asp-D-Ala-D-Tyr-D-Thr-D-Pro-D-Pro-D-Val-D-Ala-D-Met).

According to additional aspect, the present invention provides a pharmaceutical composition comprising at least one synthetic peptide according to the invention, the peptide comprising an analogue of VDAC1-derived peptide, the VDAC1-derived peptide is capable of inducing apoptosis in cancerous cells and consists of 5-26 contiguous amino acids, wherein the analogue is retro modified and partially or completely inverso modified with respect to said VDAC1-derived peptide and optionally a pharmaceutically acceptable carrier, diluents, salt or excipient.

According to certain exemplary embodiments, the pharmaceutical composition comprising at least one synthetic peptide having an amino acid sequence selected from the group consisting of SEQ ID NO:14, SEQ ID NO:15 and SEQ ID NO:16. Each possibility represents a separate embodiment of the present invention.

According to certain exemplary embodiments, the pharmaceutical composition comprises a synthetic peptide having the amino acid sequence set forth in SEQ ID NO:14.

According to other exemplary embodiments, the pharmaceutical composition comprising at least one synthetic peptide consisting of amino acid sequence selected from the group consisting of SEQ ID NO:14, SEQ ID NO:15 and SEQ ID NO:16. Each possibility represents a separate embodiment of the present invention.

According to certain exemplary embodiments, the pharmaceutical composition comprises a synthetic peptide consisting of the amino acid sequence set forth in SEQ ID NO:14.

According to certain embodiments the pharmaceutical composition comprising the synthetic peptide comprising the analogue of VDAC1-derived peptides according to the present invention further comprises at least one shielding particle. In certain embodiments the shielding particle comprises polyethyleneglycol (PEG) and/or lipids and/or Poly (D,L-lactide-co-glycolide) (PLGA).

According to additional embodiments the pharmaceutical composition comprises encapsulated synthetic peptide comprising the analogue of VDAC1-derived peptide according to the present invention. In certain embodiments the synthetic peptide is encapsulated into a vesicle, or into immunoliposomes.

The synthetic peptides of the invention and pharmaceutical compositions comprising same are affective in inducing apoptosis and/or cell death. Furthermore, as exemplified herein below, the synthetic peptides of the invention are more effective in inducing death of cells exhibiting high metabolic activity, including cancer cells compared to cells with normal metabolic activity, including corresponding healthy cells.

According to additional aspect, the synthetic peptides of the invention described herein and pharmaceutical compositions comprising same are for use in inhibiting deleterious cell proliferation. According to certain embodiments, the pharmaceutical compositions are for use in treating a disease associated with aberrant apoptosis and/or cell hyper-proliferation.

According to yet further aspect, the present invention provide a method for inhibiting deleterious cell proliferation, comprising administering to a subject in need thereof a therapeutically effective amount of the synthetic peptides of the invention or a pharmaceutical composition comprising same.

According to additional aspect, the present invention provides a method for treating a subject suffering from a disease associated with aberrant apoptosis and/or cell hyper-proliferation comprising administering to the subject a therapeutically effective amount of the synthetic peptides of the invention or a pharmaceutical composition comprising same.

According to certain embodiments, the disease associated with aberrant apoptosis and/or cell hyper-proliferation is cancer. According to certain exemplary embodiments, the cancer is selected from the group consisting of leukemia, including chronic lymphocytic leukemia (CLL), liver cancer, glioma, including glioblastoma, lung cancer, prostate cancer, pancreas cancer and melanoma. Each possibility represents a separate embodiment of the present invention.

According to certain embodiments, the cancer is leukemia. According to other embodiments, the cancer is CLL. According to yet additional embodiments, the cancer is glioblastoma. According to other embodiments, the cancer is liver cancer.

Unexpectedly, the synthetic peptides of the invention were also found to be effective in preventing and treating non-alcoholic fat liver diseases (NAFLD), particularly non-alcoholic steatosis and non-alcoholic steohepatitis (NASH).

According to additional aspect, the present invention provides a method for preventing and/or treating a non-alcoholic fatty liver disease (NAFLD) and/or symptom associated with NAFLD, the method comprises administering to a subject in need thereof a therapeutically effective amount of the synthetic peptides of the invention or a pharmaceutical composition comprising same.

According to yet a further aspect, the synthetic peptides of the invention described herein and pharmaceutical compositions comprising same are for use in treating a non-alcoholic fatty liver disease (NAFLD) and/or a symptom associated with NAFLD.

According to certain embodiments, the NAFLD is selected from the group consisting of non-alcoholic steatosis and non-alcoholic steohepatitis (NASH). According to some embodiments, the symptom associated with NAFLD is selected from the group consisting of fat droplet accumulation, inflammation, fibrosis, hepatocyte cell death and any combination thereof.

It is to be understood that any combination of each of the aspects and the embodiments disclosed herein is explicitly encompassed within the disclosure of the present invention. Other objects, features and advantages of the present invention will become clear from the following description and drawings.

DETAILED DESCRIPTION OF THE INVENTION

Figure 1:
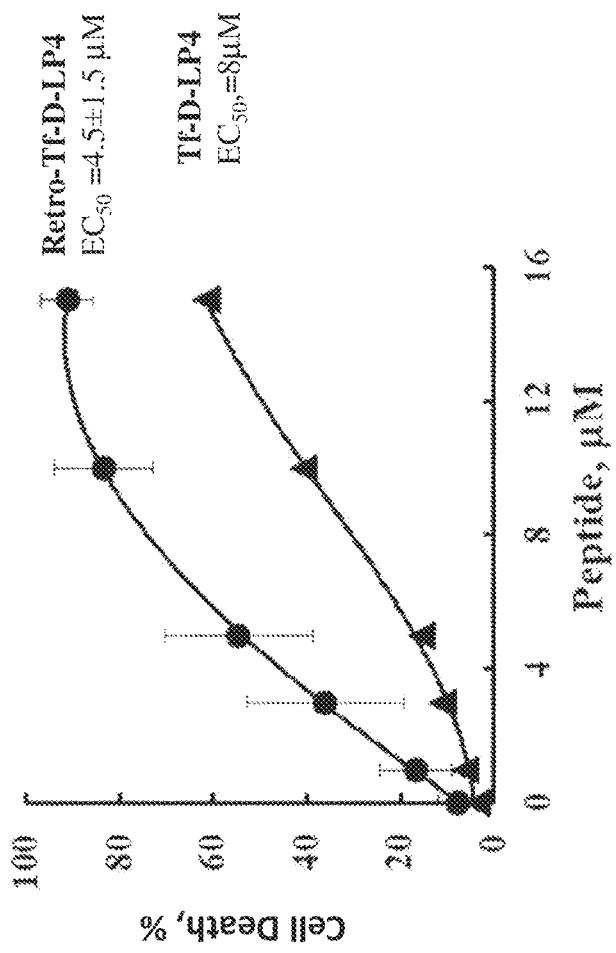
FIG. 1 shows induction of leukemia cell death by a synthetic peptide comprising a VDAC-1 derived peptide LP4 (designated Tf-D-LP4) compared to the Retro-Tf-D-LP4 peptide. Cell line used was THP1—a human monocytic cell line derived from an acute monocytic leukemia (AML) patient.

The present invention provides synthetic peptides comprising retro-inverso analogues of peptides derived from VDAC1 that preserve and even have improved activity as well as new activities compared the non-modified peptides. In addition, the retro-inverso analogues have improved solubility and stability, are capable of crossing the blood brain barrier and are thus highly suitable to be used as therapeutic peptides.

The terms "VDAC1" and "hVDAC1" are used herein interchangeably and refer to the human voltage-depended anion channel isoform 1 (hVDAC1) of a highly conserved family of mitochondrial porin. Four VDAC isoforms, encoded by three genes, are known to date; as used herein, the terms "VDAC1" and human "hVDAC1" refer to a 283 amino acid protein (NP_003365).

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. Specific peptides of the present invention are preferably utilized in β-hairpin form.

According to one aspect, the present invention provides a synthetic peptide comprising an analogue of VDAC1-based peptide, the VDAC1-based peptide is capable of inducing apoptosis in cancerous cells and consists of 5-26 contiguous amino acids, wherein the analogue is retro modified and partially or completely inverso modified with respect to the VDAC1-derived peptide.

As used herein, the terms "analogue of VDAC1-derived peptide" or "analogue of VDAC1-based peptide" refer to a synthetic peptide molecule capable of at least mimicking the induction of cancerous cell death of the native peptide derived from VDAC1 with respect to which it is modified.

As used herein, the term "retro modified" refers to a peptide analogue which is made up of L-amino acids in which the amino acid residues are assembled in opposite direction in respect to the peptide from which it is retro modified.

As used herein, the term "inverso modified" refers to a peptide analogue which is made up of at least one D-amino acids in which the amino acid residues are assembled in the same direction in respect to the peptide from which it is inverso modified. A partially inverso modified analogue refers to a peptide comprising at least one D-amino acid. A completely inverso modified analogue refers to a peptide made up of D-amino acids.

As used herein, the term "retro-inverso" modified refers to a peptide analogue which is made up of D-amino acids in which the amino acid residues are assembled in the opposite direction in respect to the peptide from which it is retro-inverso modified.

According to certain embodiments, the VDAC1-derived peptide consists of the amino acid sequence set forth in any one of SEQ ID NO:1 and SEQ ID NO:4. According to certain embodiments, the VDAC1-derived peptide consists of the amino acid sequence set forth in SEQ ID NO:1. According to certain additional embodiments, the VDAC1-derived peptide consists of the amino acid sequence set forth in SEQ ID NO:4.

According to certain exemplary embodiments, the analogue of VDAC1-derived peptide is retro-inverso analogue with respect to SEQ ID NO:1. According to these embodiments, the analogue of VDAC1 derived peptide consists of the amino acids sequence set forth in SEQ ID NO:2, wherein all the amino acids are D-amino acids to form SEQ ID NO:3.

According to certain additional exemplary embodiments, the analogue of VDAC1-derived peptide is retro-inverso analogue with respect to SEQ ID NO:4. According to these embodiments, the analogue of VDAC1-derived peptide consists of the amino acids sequence set forth in SEQ ID NO:5, wherein all the amino acids are D-amino acids To form SEQ ID NO:6.

According to certain embodiments, the synthetic peptide further comprises a cell recognition and/or localization moiety. According to some embodiments, the cell localization moiety increases the permeability of the synthetic peptide. "Permeability" refers to the ability of an agent or substance to penetrate, pervade, or diffuse through a barrier, membrane, or a skin layer. A "cell permeability moiety" or a "cell-penetration moiety" or "cell permeability enhancing moiety" refers to any molecule known in the art which is able to facilitate or enhance penetration of molecules through membranes. Non-limiting examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides; nanoparticles and liposomes.

According to certain exemplary embodiments, the recognition and/or localization moiety is a peptide cell penetration enhancing moiety. Such peptides, typically referred to as Cell Penetrating Peptides or Cell Penetration Peptides (CPPs), consists of short peptide sequences that rapidly translocate molecules, including large molecules into the cell interior in a seemingly energy- and sometimes receptor-independent manner. CPPs have low toxicity and a high yield of delivery. Exemplary CPPs are the Antp domain (having the amino acid sequence set forth in SEQ ID NO:9), the HIV-1 transcriptional factor TAT, VP22 from HSV-1. The transferrin receptor (TfR) functions in cellular iron uptake through its interaction with transferrin. This receptor is an attractive molecule for the targeted therapy of cancer since it is upregulated on the surface of many cancer types and is efficiently internalized. Tf is a peptidic sequence recognized by transferrin receptor having the amino acid sequence set forth in SEQ ID NO:7. Unexpectedly, the present invention now shows that a retro analogue of the transferrin receptor binding domain, having the amino acid sequence set forth in SEQ ID NO:8 may be also used as cancer cell recognition and penetrating moiety.

According to certain exemplary embodiments, the recognition and/or localization peptide comprises SEQ ID NO:7 or a retro analogue thereof, having the amino acid sequence set forth in SEQ ID NO:8. According to additional exemplary embodiments, the recognition and/or localization peptide consist of SEQ ID NO:7 or a retro analogue thereof, consisting of the amino acid sequence set forth in SEQ ID NO:8.

According to other embodiments, the recognition and/or localization peptide is a partially inverso modified analogue of SEQ ID NO:7 or of SEQ ID NO:8. According to additional embodiments, the recognition and/or localization peptide is a completely inverso modified analogue of SEQ ID NO:7 or of SEQ ID NO:8.

According to certain additional exemplary embodiments, the recognition and/or localization peptide comprises SEQ ID NO:9 or a retro analogue thereof, having the amino acid sequence set forth in SEQ ID NO:10. According to additional exemplary embodiments, the recognition and/or localization peptide consist of SEQ ID NO:9 or a retro analogue thereof, consisting of the amino acid sequence set forth in SEQ ID NO:10. According to other embodiments, the recognition and/or localization peptide is a partially inverso modified analogue of SEQ ID NO:9 or of SEQ ID NO:10. According to additional embodiments, the recognition and/ or localization peptide is a completely inverso modified analogue of SEQ ID NO:9 or of SEQ ID NO:10.

According to certain embodiments, the synthetic peptides of the invention comprises the amino acids sequences SWTWE (SEQ ID NO:11) and KWTWK (SEQ ID NO:12), together the "Tryptophan (Trp) zipper peptide" or a retro analogue(s) thereof, each independently located at the C- or N-terminus of the analogue of VDAC1 derived peptide.

According to certain embodiments, the Trp zipper peptide or a retro-analogue thereof is all L-stereomeric peptide. According to other embodiments, the Trp zipper peptide or a retro-analogue thereof is partially inverso modified. According to additional embodiments, the Trp zipper peptide or a retro-analogue thereof is completely inverso modified containing only D-amino acids. According to some embodiments, the retro-analogue of the Trp zipper peptide comprises the amino acid sequence set forth in SEQ ID NO:13 (EWTWS). According to yet additional embodiments, the Trp zipper peptide comprises retro-inverso analogue of SEQ ID NO:11, SEQ ID NO:12 or the combination thereof.

According to additional exemplary embodiments, the present invention provides a synthetic peptide comprising a retro-inverso analogue of SEQ ID NO:1 flanked by Trp zipper having the amino acids sequence set forth in SEQ ID NO:12 at its N-terminus and the amino acids sequence set forth in SEQ ID NO:13 at its C-terminus further comprising a recognition and/or localization peptide having the amino acids sequence set forth in SEQ ID NO:8. According to some embodiments, the synthetic peptide comprises the amino acids sequence set forth in SEQ ID NO:19 (Lys-Trp-Thr-Trp-Lys-D-Asn-D-Ser-D-Asn-D-Gly-D-Ala-D-Thr-D-Trp-D-Ala-D-Leu-D-Asn-D-Val-D-Ala-D-Thr-D-Glu-D-Leu-D-Lys-D-Lys-Glu-Trp-Thr-Trp-Ser-His-Arg-Pro-Tyr-Ile-Ala-His). According to certain exemplary embodiments, the peptide consists of SEQ ID NO:19.

An exemplary sequence of a synthetic peptide of the invention comprises from the N- to C-terminus a Trp zipper peptide having the amino acid sequence set forth in SEQ ID NO:12, wherein the amino acids are D-amino acids, followed by a retro-inverso analogue of SEQ ID NO:1 (having the amino acid sequence of SEQ ID NO:2 wherein the amino acids are D-amino acids to form SEQ ID NO:3) followed by a Trp zipper peptide having the amino acid sequence set forth in SEQ ID NO:13, wherein the amino acids are D-amino acids, followed by a retro-analogue of a the Tf recognition and/or localization peptide having the amino acids sequence set forth in SEQ ID NO:7 (the retro analogue having the amino acid sequence set forth in SEQ ID NO:8). The peptide, referred to herein interchangeably as Retro-Tf-D-LP4, retro-inverso peptide, retro-inverso Tf-D-LP4 or retro-inverse Tf-D-LP4 consists of the amino acid sequence D-Lys-D-Trp-D-Thr-D-Trp-D-Lys-D-Asn-D-Ser-D-Asn-D-Gly-D-Ala-D-Thr-D-Trp-D-Ala-D-Leu-D-Asn-D-Val-D-Ala-D-Thr-D-Glu-D-Leu-D-Lys-D-Lys-D-Glu-D-Trp-D-Thr-D-Trp-D-ser-His-Arg-Pro-Tyr-Ile-Ala-His (SEQ ID NO:14).

An additional exemplary sequence of a synthetic peptide of the invention comprises from the N- to C-terminus a retro analogue of Antp cell penetration peptide having the amino acids sequence set forth in SEQ ID NO:9 (the retro analogue having the amino acid sequence set forth in SEQ ID NO:10) followed by a retro-inverso analogue of SEQ ID NO:4 (having the amino acid sequence of SEQ ID NO:5 wherein the amino acids are D-amino acids to form SEQ ID NO:6). The peptide, referred to herein as "retro-inverso N-terminal" or Retro-D-N-Ter consists of the amino acid sequence Lys-Lys-Trp-Lys-Met-Arg-Arg-Asn-Gln-Phe-Trp-Ile-Lys-Ile-Gln-Arg-D-Leu-D-Gly-D-Phe-D-Gly-D-Tyr-D-Gly-D-Lys-D-Thr-D-Phe-D-Val-D-Asp-D-Arg-D-Ala-D-Ser-D-LyD-Gly-D-Leu-D-Asp-D-Ala-D-Tyr-D-Thr-D-Pro-D-Pro-D-Val-D-Ala-D-Met (SEQ ID NO:15).

According to certain embodiments, the C-terminus of the peptides of the invention may be amidated, acylated, reduced or esterified. Each possibility represents a separate embodiment of the present invention.

As used herein the term "apoptosis" or "apoptotic cell death" refers to programmed cell death which can be characterized by cell shrinkage, membrane blebbing and chromatin condensation culminating in cell fragmentation. Cells undergoing apoptosis also display a characteristic pattern of DNA cleavage. Alternatively, apoptosis can be characterized indirectly by changes in the activity or expression of members of the apoptotic pathway, e.g. increased mitochondrial release of cytochrome c. A non-limiting example of apoptosis-inducing reagents known in the art includes actinomycin D, antibiotic A-23187, b-lapachone, Camptothecin, ceramide, curcumin, dexamethasone, etoposide (Etopophos®, Vepesid®), Hypericin, prostaglandin A2, S-Nitrosoglutathione, staurosporin, sulindac sulfide, sulindac sulfone, paclitaxel (Taxol®), vinblastine sulfate, vincristine sulfate, 15(S)-HPETE, 4-hydroxyphenyl retinamide, betulinic acid and the like.

As exemplified hereinbelow, the Retro-Tf-D-LP4 is highly active in inducing cancer cell death. Furthermore, as exemplified with the human primary glioblastoma cell line U-87 (FIG. 5), the synthetic peptide comprising the retro-inverso analogue of VDAC-1 derived peptide LP4 was much more effective in inducing cancer cell death compared to non-malignant Madin-Darby Canine Kidney epithelial cells.

The Retro-Tf-D-LP4 peptide comprises a retro analogue of the transferrin-receptor binding domain. Unexpectedly, the present invention now shows that the retro-analogue has equivalent recognition and/or localization activity as the native peptide.

As further exemplified herein below, the Retro-Tf-D-LP4 was shown to be effective in inhibiting the development of cancer in vivo. Two models were used; one showing the effect of Retro-TF-D-LP4 on the development of brain tumor intracranial xenograft and the other showing the effect of the peptide on Diethylnitrosoamine (DEN)-induced liver cancer.

In the brain orthotopic tumor model glioblastoma U-87 MG cells were engrafted into nude mice brains. The mice treated i.v. with free Retro-Tf-D-LP4 peptide or with PLGA nanoparticles-encapsulated peptide showed significantly lower tumor volume (by up to 90% for free peptide, FIG. 11). These results suggest that the peptide most likely crosses the BBB also when in free form. Without wishing to be bound to any specific theory or mechanism of action, crossing the BBB may be mediated by the TfR recognized sequence linked to the VDAC a derived analogue, although the Tf domain is also in a retro-configuration as described hereinabove.

Figure 12A:
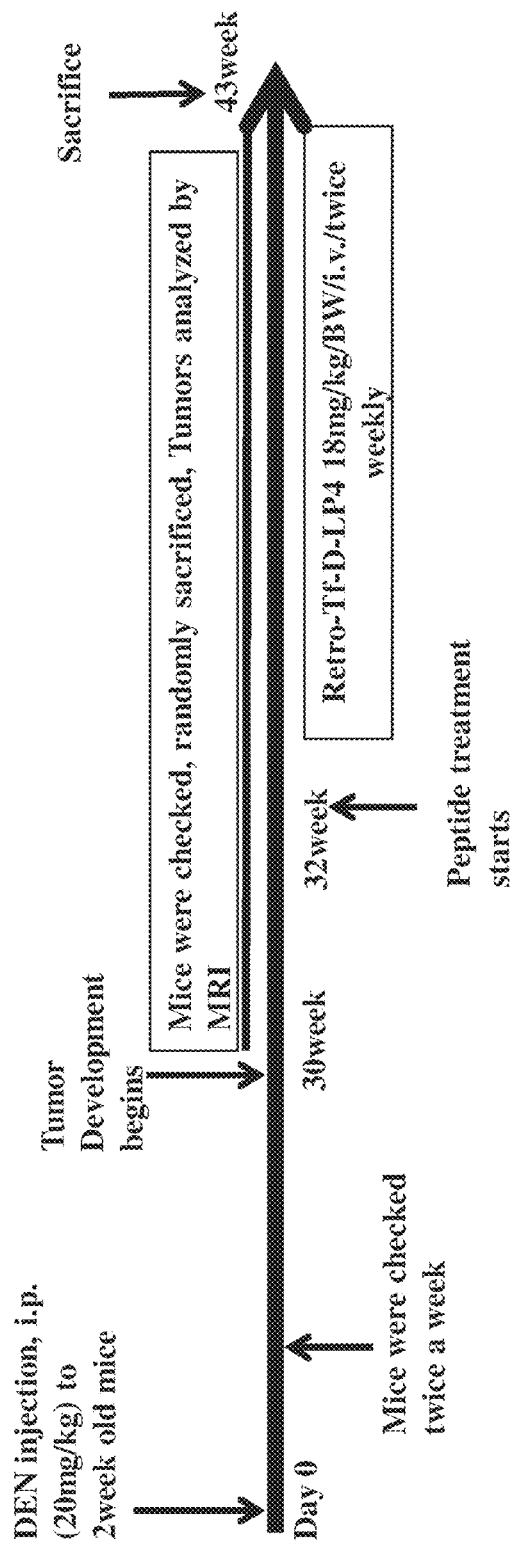
FIG. 12A shows schematic presentation of the experiment protocol for inhibition of tumors development in the liver as induced by treating mice with DEN (DEN-induced liver cancer) by the Retro-Tf-D-LP4 peptide.
Figure 12C:
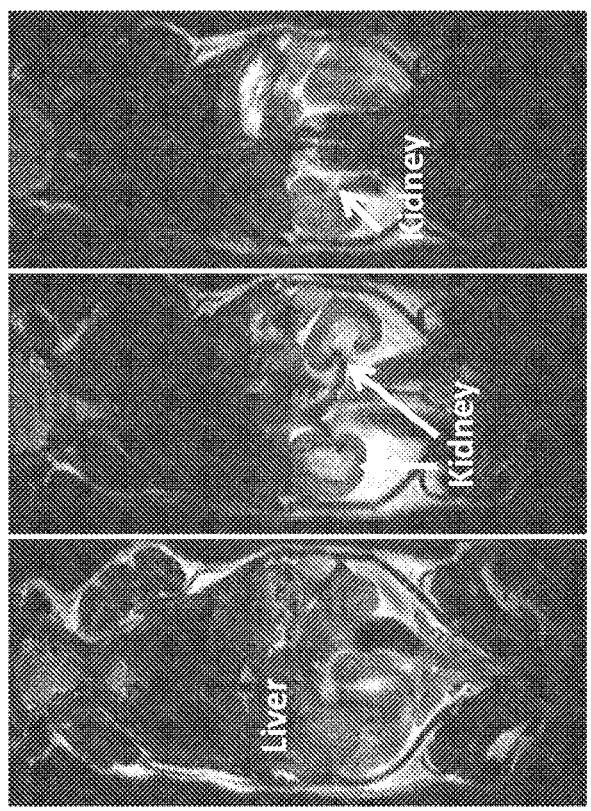
FIG. 12C shows MRI imaging of livers from Retro-TF-D-LP4 peptide treated mice.
Figure 12B:
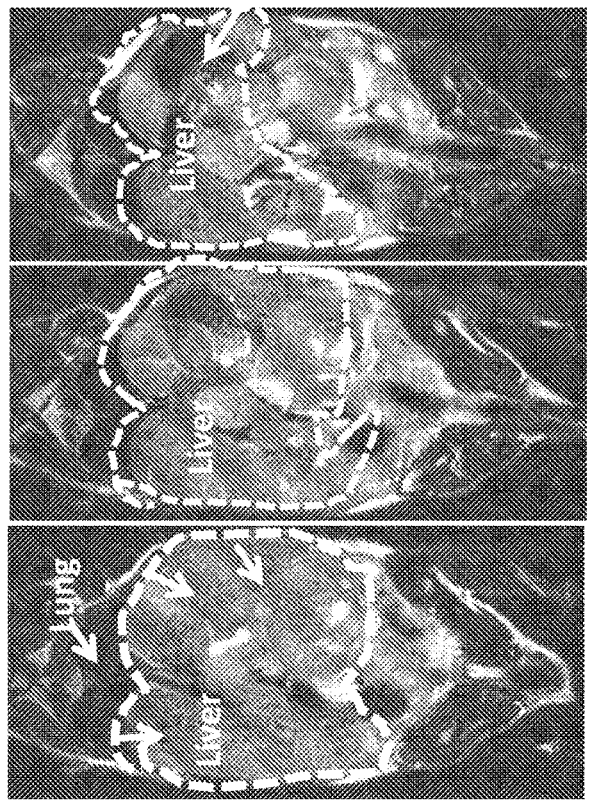
FIG. 12B shows MRI imaging of livers from control untreated mice.
Figure 12D:
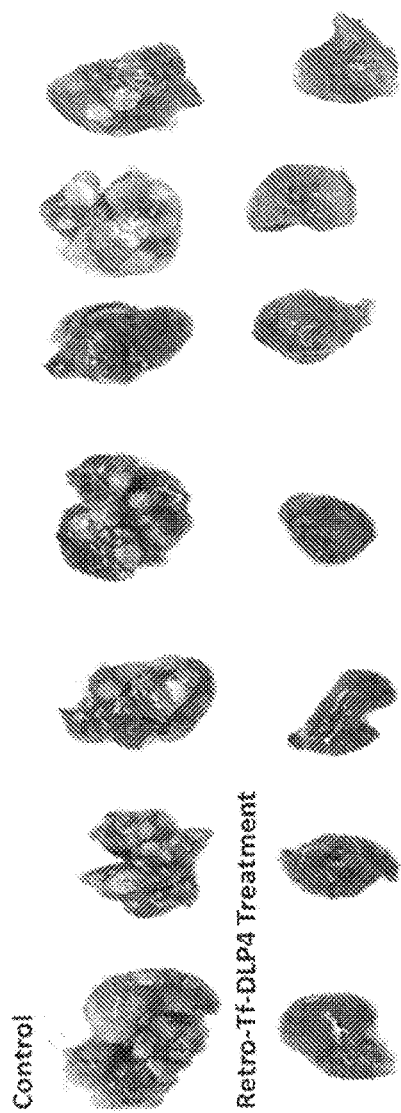
FIG. 12D shows photographs of livers from DEN-treated mice of control (untreated) and Retro-TF-D-LP4 peptide treated group.
Figure 12E:
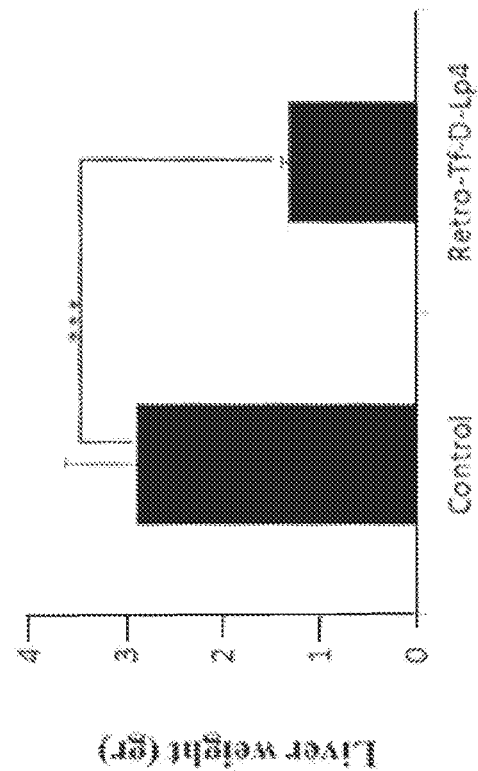
FIG. 12E shows liver weight of control and Retro-TF-D-LP4 peptide treatment group. Results=mean±SEM (n=5) (p: ***≤0.001)

In the DEN-induced hepatocellular carcinoma (HCC) mice were injected intravenously with the Retro-Tf-D-LP4 peptide or with a control solution (2% DMSO in HBSS). In the untreated, control group mice livers showed high number of tumor nodules (FIG. 12B, 12D), whereas in mice treated with the peptide no tumor nodules were observed (FIG. 12C, 12D). In the control group livers were big in size and weight comparing to livers from mice treated with the Retro-Tf-D-LP4 peptide (FIG. 12E). These results show that the peptide inhibited tumor development.

Unexpectedly, the retro-inverso peptides of the invention further exhibited significant activity in preventing and/or treating nonalcoholic steatohepatitis (NASH). The model used for steatohepatitis/NASH (STAM) was based on HFD-32, where fatty liver disease was induced by caloric excess as occurs in most humans with NASH, displaying all of the physiological, metabolic, histological, and clinical endpoints of human NASH. Upon initiation of HFD-32 feeding, the mice developed steatohepatitis with fat droplets accumulation in hepatocytes, scattered inflammatory cell infiltrates, ballooning and Mallory-Denk bodies, fibrosis and finally HCC nodules (FIGS. 13-20). VDAC1-based peptide, Retro-Tf-D-LP4, intravenously administrated eliminated or highly reduced all these liver pathogeneses. Livers from peptide-treated mice showed very low fatty deposits, inflammatory cell infiltrates or collagen fibers (FIGS. 13-20).

According to additional aspect, the present invention provides a pharmaceutical composition comprising at least one synthetic peptide comprising an analogue of VDAC1-derived peptide, the VDAC1-derived peptide is capable of inducing apoptosis in cancerous cells and consists of 5-26 contiguous amino acids, wherein the analogue is retro modified and partially or completely inverso modified with respect to the VDAC1-derived peptide and optionally a pharmaceutically acceptable carrier, diluents, salt or excipient.

The term "pharmaceutically acceptable carrier" refers to a vehicle which delivers the active components to the intended target and which does not cause harm to humans or other recipient organisms. As used herein, "pharmaceutical" will be understood to encompass both human and animal pharmaceuticals. Useful carriers include, for example, water, acetone, ethanol, ethylene glycol, propylene glycol, butane-1, 3-diol, isopropyl myristate, isopropyl palmitate, or mineral oil. Methodology and components for formulation of pharmaceutical compositions are well known, and can be found, for example, in Remington's Pharmaceutical Sciences, Eighteenth Edition, A. R. Gennaro, Ed., Mack Publishing Co. Easton Pa., 1990.

The pharmaceutical compositions can also comprise other optional materials, which may be chosen depending on the carrier and/or the intended use of the composition. Additional components include, but are not limited to, antioxidants, chelating agents, emulsion stabilizers, e.g., carbomer, preservatives, e.g., methyl paraben, fragrances, humectants, e.g., glycerin, waterproofing agents, e.g., PVP/Eicosene Copolymer, water soluble film-formers, e.g., hydroxypropyl methylcellulose, oil-soluble film formers, cationic or anionic polymers, and the like Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes, the compositions of the present invention may be administered orally due to the high activity observed for the stable retro-inverso peptides of the invention. In addition, novel methods are being used in order to design and provide metabolically stable and oral bioavailable peptidomimetic analogues.

The pharmaceutical composition of this invention may be administered by any suitable means, such as topically or parenterally including intranasal, subcutaneous, intramuscular, intravenous, intra-arterial, intraarticular, or intralesional administration.

The molecules of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art. (See, for example, Ansel et al., 1990 and Gennaro, 1990). In addition, if desired, the composition can contain minor amounts of auxiliary substances such as wetting or emulsifying agents, pH buffering agents.

As exemplified herein (FIG. 9) the present invention now shows that the synthetic peptide comprising a retro-inverso analogue of VDAC1-derived peptide is highly soluble in physiologically compatible solutions. This solubility is a significant advantage of the retro-inverso peptides of the invention over the hitherto known peptides derived from VDAC1, making the peptides highly compatible for use as a drug.

According to additional aspect, the present invention provides a method for treating a subject suffering from a disease associated with aberrant apoptosis and/or cell hyper-proliferation comprising administering to the subject a therapeutically effective amount of the synthetic peptides of the invention or a pharmaceutical composition comprising same.

According to certain embodiments, the disease associated aberrant apoptosis and/or cell hyper-proliferation is cancer. According to certain exemplary embodiments, the cancer is selected from the group consisting of glioma, including glioblastoma; liver cancer, including hepatocellular carcinoma; leukemia, including chronic lymphocytic leukemia (CLL); pancreas and breast cancer and melanoma. Each possibility represents a separate embodiment of the present invention.

According to additional aspect, the present invention provides a method for preventing and/or treating a non-alcoholic fatty liver disease (NAFLD) and/or symptom associated with NAFLD, the method comprises administering to a subject in need thereof a therapeutically effective amount of the synthetic peptides of the invention or a pharmaceutical composition comprising same.

As used herein, the term "treating" means remedial treatment, and encompasses the terms "reducing", "suppressing", "ameliorating" and "inhibiting", which have their commonly understood meaning of decreasing or arresting tumor growth and/or decreasing or arresting cancer cell proliferation and/or decreasing the tumorigenicity of cancer stem cells and/or decreasing or arresting the development of NAFLD and symptoms associated with NAFLD.

According to certain embodiments, the peptides of the invention are for prophylactic use, particularly for preventing and/or reducing the progress of NAFLD, particularly non-alcoholic steatosis and non-alcoholic steohepatitis (NASH).

The term "therapeutically effective amount" as used herein refers to an amount of the pharmaceutical composition that when administered to a subject is capable of exerting anticancer activity and/or decreasing or arresting NAFLDs and associated symptoms. According to yet a further aspect, the synthetic peptides of the invention described herein and pharmaceutical compositions comprising same are for use in treating a non-alcoholic fatty liver disease (NAFLD) and/or a symptom associated with NAFLD.

According to certain embodiments, the NAFLD is selected from the group consisting of non-alcoholic steatosis and non-alcoholic steohepatitis (NASH). According to some embodiments, the symptom associated with NAFLD is selected from the group consisting of fat droplet accumulation, inflammation, fibrosis, hepatocyte cell death and any combination thereof.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Material and Methods
Cell Culture
THP-1, BNL1ME, GL-261, PANC-1, PANC-2, B16F10.0, MDCK, U-87MG, U-251MG, U-118MG, LN-18 cell lines were maintained at 37° C. and 5% $CO_2$ in the recommended culture medium with 10% FCS, penicillin (100 u/ml) and streptomycin (100 μg/ml).
Cells Treatment with VDAC1-Based Peptides and Cell Death Analysis Cells in suspension were counted ($2\times10^6$/ml) and treated on the same day whereas adherent cells were counted and seeded ($1.5\text{-}2\times10^5$/ml) in 12 wells plate 16-24 h before treatment. Cells in suspension or adherent cells were incubated in serum-free medium (200 μl or 500 μl, respectively) with various concentrations of peptide of interest (for 90 min or 6 h, respectively) at 37° C. in the presence of 5% $CO_2$. Cells were collected (adherent cells by trypsinization), centrifuged (1500×g, 5 min), washed once with PBS and analyzed for cell death using propidium iodide (PI) staining and flow cytometer (Beckton-Dickinson, San Jose, Calif.) and BD CellQuest Pro software.
Peptides The control synthetic peptide was composed of the VDAC1-derived peptide having the amino acid sequence set forth in SEQ ID NO:1 (designated LP4), wherein the amino acids of SEQ ID NO:1 are D-amino acids, flanked by the Trp zipper having the amino acid sequence set forth in SEQ ID NO:11 at its N-terminus and the amino acid sequence set forth in SEQ ID NO:12 at its C-terminus, the amino acids being in D-configuration and a Tf localization peptide having the amino acid sequence set forth in SEQ ID NO:7 linked to the N-terminus of SEQ ID NO:11, to form SEQ ID NO:17 (His-Ala-Ile-Tyr-Pro-Arg-His-D-Ser-D-Trp-D-Thr-D-Trp-D-Glu-D-Lys-D-Lys-D-Leu-D-Glu-D-Thr-D-Ala-D-Val-D-Asn-D-Leu-D-Ala-D-Trp-D-Thr-D-Ala-D-Gly-D-Asn-D-Ser-D-Asn-D-Lys-D-Trp-D-Thr-D-Trp-D-Lys). The peptide is designated Tf-D-LP4.

The examined synthetic peptide designated Retro-Tf-D-LP4 comprises the amino acid sequence set forth in SEQ ID NO:14 composed as described hereinabove.

The peptides were synthesized by GL Biochem (Shanghai, China) to >95% purity. The peptides were dissolved as follows: 2 mg of Tf-D-LP4 or Retro-Tf-D-LP4 were dissolved in 5 μl of 100% DMSO to yield solution with peptide concentration of 400 mg/ml (97.36 mM) and the solutions were further incubated at 37° C. water bath for 30 minutes. Then the solutions were diluted to peptide concentration of 20 mg/ml (4.86 mM) by adding while mixing 95 µl of distilled water and the diluted solutions were incubated in 37° C. water bath for 30 minutes to allow further solubilization until the solutions became clear. The peptide solutions were then centrifuged for 5 min at 15,000 g and the supernatant of each preparation was transferred to fresh Eppendorf tube with low binding capacity. Aliquots of the obtained solution were taken for further analysis of peptide concentration.

Propidium Iodide (PI) Staining

PI solution was diluted with PBS to a final concentration of 0.5 mg/ml. 2.5 µl of the PI solution were added to each FACS tube, and the tubes were vortexed gently to homogenize the cell suspension. Cell viability was measured in the FACS channel FL3 and data were analyzed using CellQuest Pro software.

Hematoxylin/Eosin (H&E), Oil Red O; Masson Trichrome and Sirius Red Staining

Hematoxylin/Eosin (H&E) staining of paraffin-embedded liver sections (5 µm thickness) was performed using standard protocol.

Oil Red O staining is an assay performed to stain lipid droplets in cells. Cryosections prepared by embedding fresh liver specimen in O.C.T compound (Scigen, USA) were washed gently with 60% isopropanol and stained with the working solution of 0.5 g Oil Red O (BDH chemicals, England) in 60% isopropanol for 15 min. The stained sections were washed with distilled water several times to remove unincorporated dye. Then, the samples were counterstained with hematoxylin for 5 min. Results were examined using a light microscope. Lipid droplets appear red and nuclei appear blue Masson trichrome (Bio optica, Italy) staining was carried out as described previously (Martinello T et al. 2015. Histol Histopathol. 30(8), 963-969). By this staining, collagen appears blue, muscle fibers appear red and nuclei appear black/blue.

Sirius red (Sigma, USA) Staining was performed on paraffin-embedded liver sections as described previously (Zhang Y et al. 2014. Hepatology 60, 919-930). Briefly, liver tissue fixed and embedded in paraffin sections were stained with a 0.1% Sirius red-picric solution. Sections were washed rapidly with acetic acid and photographed under a light microscope. Collagen appears in red on a pale yellow background.

Xenograft Experiments

For the intracranial-orthotopic xenograft mouse model, U-87MG cells ($8 \times 10^4$) were engrafted into a nude mouse brain using a stereotactic device. Forty eight hours after surgery, mice were randomized into three groups (6 animals per group) and treated every third day with DMSO (1.44%), Retro-Tf-D-LP4 (10 mg/Kg) or Retro-Tf-D-LP4 (10 mg/Kg) encapsulated in PLGA nano-particles. Mice were subjected to Mill and then sacrificed. Brains were excised and processed for IHC. Tumor volume was analyzed using VivoQuant 2.10 software.

Induction of Liver Cancer

For liver cancer induction, Diethylnitrosoamine (DEN), also known as N-nitrosodiethylamine, was used. DEN is widely used as a carcinogen in experimental animal models (Shirakami Y et al. 2012. Carcinogenesis 33, 268-274; Tolba, R et al. 2015. Lab Anim 49, 59-69).

C57BL/6 mice (male) 14 day old were injected (i.p) with DEN (Sigma-Aldrich) at 20 mg/kg body weight, and were checked regularly thereafter. Mice were checked for liver tumor development by randomly scarifying 2 mice. Tumor development starts at 30 weeks. After confirmation of tumors development mice were grouped as follows: control group mice (n=12) received 50 µl of 2% DMSO in HBSS buffer intravenously; treatment group (n=12) received 18 mg/Kg Retro-Tf-D-LP4 by intravenous injection. The peptide treatment was given for three times in the first two weeks, then twice weekly up to 43 weeks. Tumor size was analyzed by MRI. At the end of the experiment, mice were sacrificed; livers were photographed and fixed in 4% formaldehyde in PBS for histopathological analysis.

Non-Alcoholic Steatohepatitis-Hepatocellular Carcinoma (NASH-HCC) Mice Model

Male and female C57Bl/6 mice were purchased from ENVIGO (Jerusalem, Israel). All mice were kept at the Animal Facilities of the Ben-Gurion University (Beer-Sheva Israel), under aseptic conditions. Steatosis-NASH-HCC was obtained as described previously (Fujii M et al. Med Mol Morphol 46, 141-152). To induce Steatosis-NASH mice were breed and two days old new born mice male were injected sub-cutaneously with streptozotocin (STZ) (200 µg/mouse) and returned back to the cage to nursing mother.

At 4 weeks of age mice were subjected to High Fat Diet (HFD-32). Liver steatotic pathology begins to develop at 6 week and NASH at 9 weeks. Mice were grouped as control (n=10) and treatment (n=10) groups and the treatment began for steatosis study at week 7 to week 9 and for NASH study at week 9 to week 12. Control group received 50 µl of 0.9% DMSO in HBSS buffer. Treatment group-1 (n=10) received Retro-Tf-D-LP4 (SEQ ID NO:14) 10 mg/kg, and treatment group-2 (n=10) received Retro-Tf-D-LP4 (SEQ ID NO:14) 18 mg/kg, all by intravenous injection. The peptide treatment was given three times a week. At the end of the experiment, mice were anesthetized with Ketamine (100 mg/kg) and Xylasine (10 mg/kg) in PBS and blood samples were taken. The chest was opened and blood was obtained from the heart. Then, mice were sacrificed by $CO_2$ inhalation. Livers were removed, photographed and weighed. Part of the liver was fixed, embedded in paraffin, sectioned, and subjected to hematoxylin/eosin (H&E) staining as described above. For Oil red staining, part of the liver was frozen in Optimal Cutting Temperature compound (O.C.T), embedded, sectioned and stained for fat content using Oil Red O staining as described above.

Blood glucose levels were measured using Accu-Check® Performa blood glucose meter (Accu-Check®).

Dietary Interventions of NASH-HCC Model Mice

Four week old male mice previously injected with STZ were separated from the mothers and feed with High Fat Diet (HFD-32) during the entire courses of the experiments. HFD-32 feed was composed of 5% egg white powder (MM Ingredients; Wimborne, UK); 6.928% lactose (PHARMA GRADE; Nelson, UK); 15.88% beef fat (saturated) powder (contain 80% beef fat) (MP Biomedical, LLC; Illkirch, France); 24.5% milk casein (Shaanxi Fuheng (SF) Biotechnology; Xi'an, China); 20% safflower oil (high oleic acid type) (Bustan aBriut; Galil, Israel); 6.45% sucrose (Sigma, St; Louis, Mo.); 0.36% choline bitartrate (BULK POWDERS, Colchester, UK); 5.5% crystalline cellulose (Sigma, St; Louis, Mo.); 0.43% L-cysteine (Source Naturals, Scotts Valley, USA); 8.25% maltodextrin (BULK POWDERS, Colchester, UK); 5% AIN93G-mineral mixture (MP Biomedical, LLC; Illkirch, France); 1.4% AIN93VX-vitamin mix (MP Biomedical, LLC; Illkirch, France) and 0.002% tertiary butyl hydroquinone (MP Biomedical, LLC; Illkirch, France). Control C57Bl/6 mice were fed with a standard chow diet.

Animal studies were performed in compliance with all applicable policies, procedures and regulatory requirements of the Institutional Animal Care and Use Committee (IA-CUC), the Research Animal Resource Center (RARC) of Ben-Gurion University and the National Institutes of Health (NIH) "Guide for the Care and Use of Laboratory Animals".

Example 1: Induction of Cell Death in Leukemia Cells

Cells of human monocytic cell line derived from an acute monocytic leukemia patient (THP-1 cells, 400,000 cells per well) were used in this experiment. Each of the control (Tf-D-LP4) and the assay retro-inverso (Retro-Tf-D-LP4) peptides at several concentrations was added to serum-free medium as described herein above and cells were incubated in the presence of each peptide type for 90 min at 37° C. in the presence of 5% $CO_2$.

As is shown in FIG. 1, both peptides induced significant cell death. Cell death by the retro-inverso peptide (Retro-Tf-D-LP4) was obtained with $EC_{50}$ of 4.5 μM compared to $EC_{50}$ of 8 μM of the control peptide (Tf-D-LP4).

Example 2: Induction of Cell Death in Liver Cancer Cells

Figure 2:
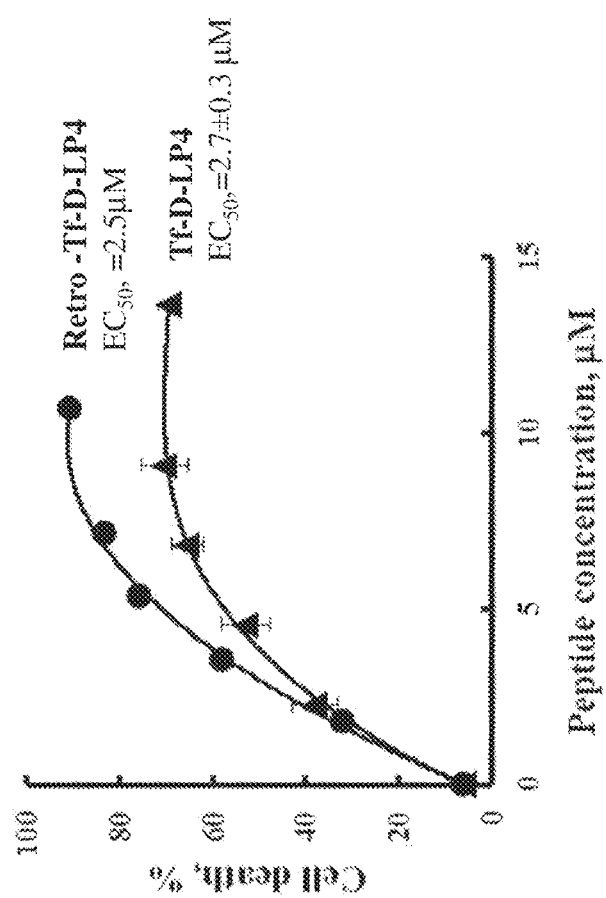
FIG. 2 shows the induction of liver cancer cell death by a synthetic peptide comprising a VDAC-1 derived peptide LP4 (designated Tf-D-LP4) compared to the Retro-Tf-D-LP4 peptide. Cell line used was BNL1ME derived from BNL CL.2 by transformation with methylcholanthrene epoxide.

FIG. 2 demonstrates the effect of the control (Tf-D-LP4) and examined retro-inverso peptide (Retro-Tf-D-LP4) on cancerous liver mouse BNL1ME cell line. Cells were incubated in a serum-free medium with each peptide type for 6 h at 37° C. in the presence of 5% $CO_2$.

As with the leukemia cells, both peptides induced massive cell death, with similar $EC_{50}$ ($EC_{50}$ of 2.5 μM and 2.7 μM for Retro-Tf-D-LP4 and Tf-D-LP4, respectively). However, higher maximal cell death induction was obtained with the retro-inverso peptide (95% compare to 70%).

Example 3: Induction of Cell Death in PANC-1 or PANC 2 Cells

The human (PANC-1) and mouse (PANC-2) cancerous pancreatic cells were used in this assay. Cells were seeded (100,000 cells/well) and treated with Retro-Tf-D-LP4 peptide in a serum-free medium for 6 h at 37° C. in the presence of 5% $CO_2$. Cell death was analyzed by PI staining and percentage of cell death was measured by Flow Cytometery.

Figure 3A:
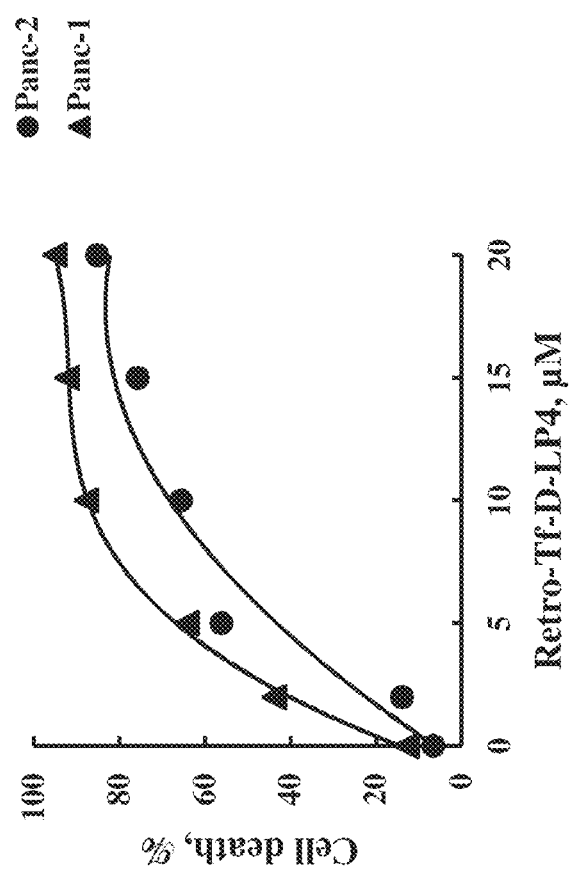
FIG. 3A shows the effect of Retro-Tf-D-LP4 on human PANC-1 cells established from a pancreatic carcinoma of ductal origin from a 56-year-old Caucasian male and on mouse PANC-2 cells established from a mouse (C57BL/6) pancreatic ductal carcinoma.

As is shown in FIG. 3A, the retro-inverso peptide (Retro-TF-D-LP4) induced cell death in both cell lines with $EC_{50}$ of about 4 μM.

Figure 3B:
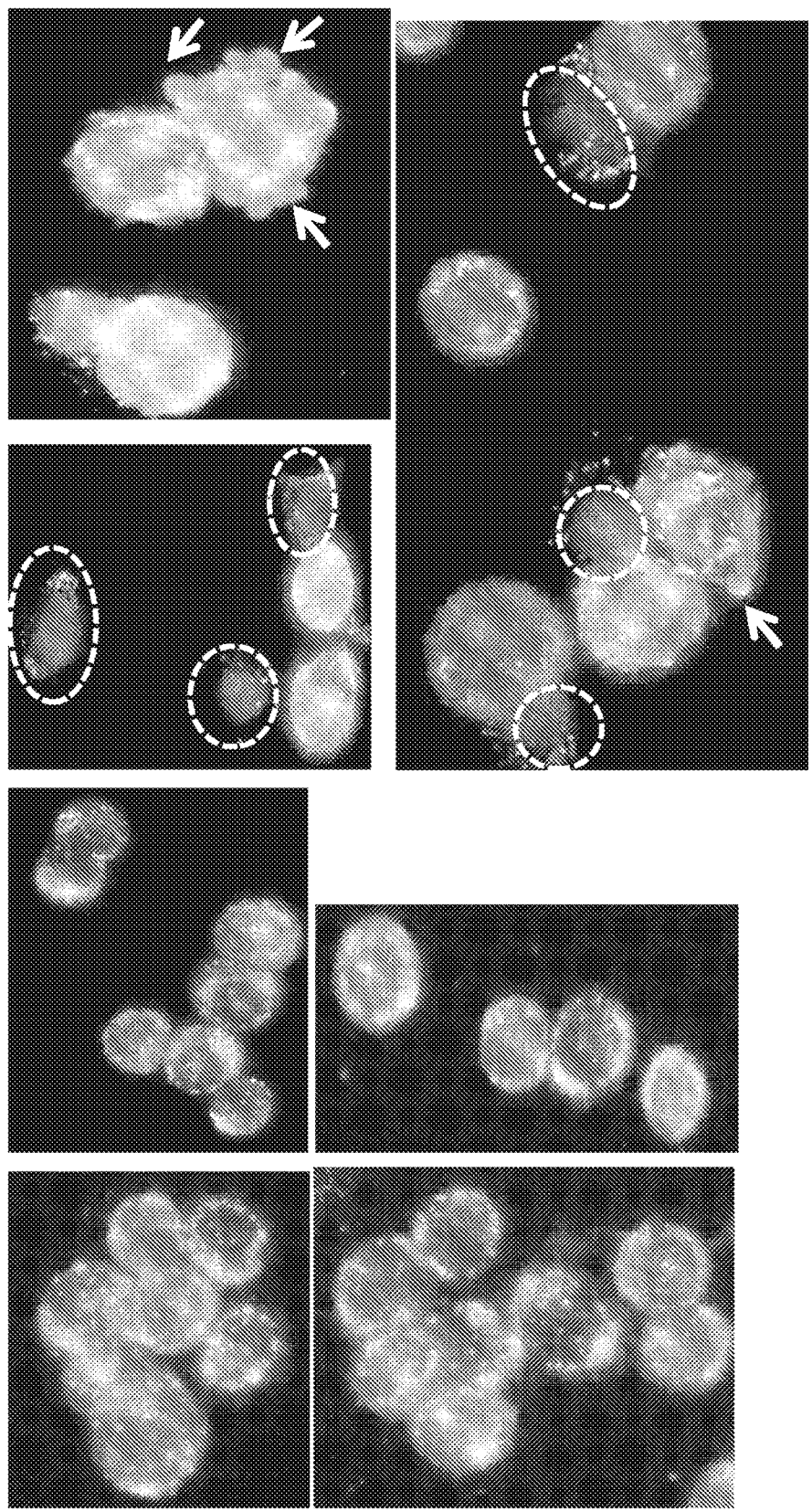
FIG. 3B shows acridine orange, ethidium bromide staining of untreated PANC-2 cells (control), PANC-2 incubated with 5% DMSO and PANC-2 cell incubated with 2 µM of the Retro-Tf-D-LP4.

FIG. 3B shows acridine orange, ethidium bromide staining of PANC-2 cells demonstrating that retro Tf-D-LP4 induces apoptosis.

Example 4: Induction of Cell Death in Melanoma Cells

B16F10.0 melanoma cells (150,000 cells/well in 12-well plate) were seeded and the day after were incubated in a serum-free medium with the indicated concentration of Retro-Tf-D-LP4 peptide for 6 h at 37° C. in the presence of 5% $CO_2$. Cell death was analyzed by PI staining and FACS.

Figure 4:
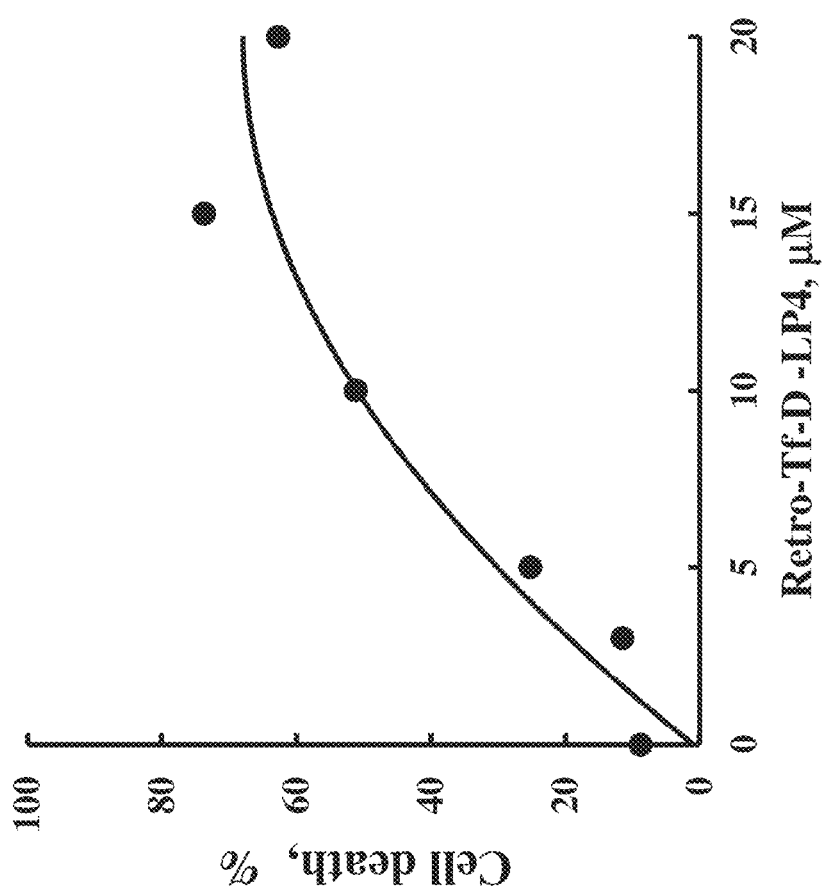
FIG. 4 shows cell death induced by the Retro-Tf-D-LP4 peptide on mouse derived B16F10.0 melanoma cancer cells.

As is shown in FIG. 4, the retro-inverso peptide (Retro-TF-D-LP4) induced concentration-depended cell death, with $EC_{50}$ of 7 μM.

Example 5: Induction of Cell Death in Mouse Glioma Cells

Mouse glioma GL-261 cells were incubated in a serum-free medium for 6 h at 37° C. in the presence of 5% $CO_2$ with the control Tf-D-LP4 or Retro-Tf-D-LP4 peptide at several concentrations and cell death was analyzed by PI staining and FACS.

Figure 5:
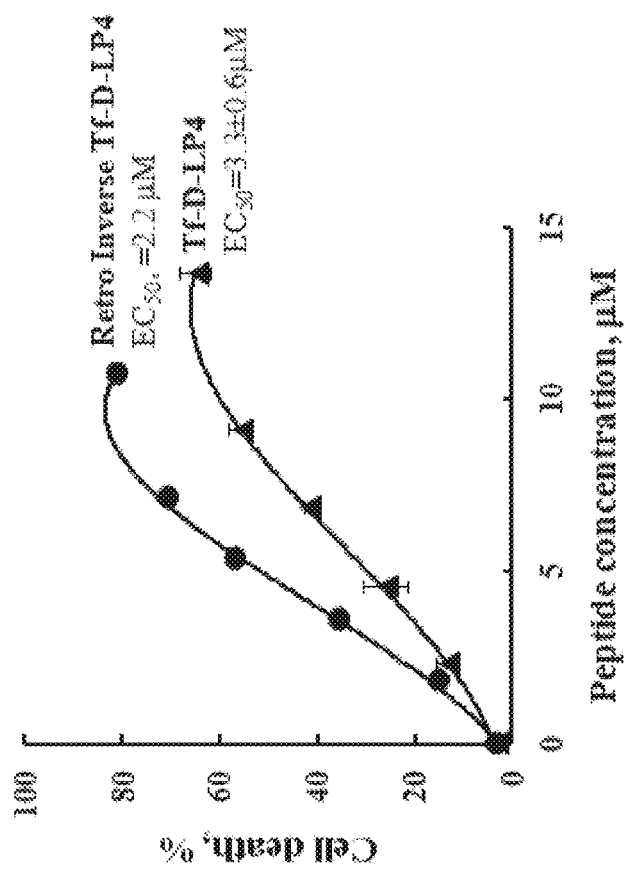
FIG. 5 shows the percentage of cell death of glioma cancer cell line U-87MG induced by a synthetic peptide comprising a VDAC-1 derived peptide LP4 (designated Tf-D-LP4) compared to the Retro-Tf-D-LP4. Cell line used was GL-261, a mouse glioma cell line.

As is shown in FIG. 5, both peptides induced significant cell death; however, induction of cell death by the retro-inverso peptide (Retro-TF-D-LP4) was significantly higher compared to the control peptide, with $EC_{50}$ of 2.2 μM compared to $EC_{50}$ of 3.3 μM of the control peptide.

Example 6: Induction of Cell Death in Glioblastoma Cells

Figure 6:
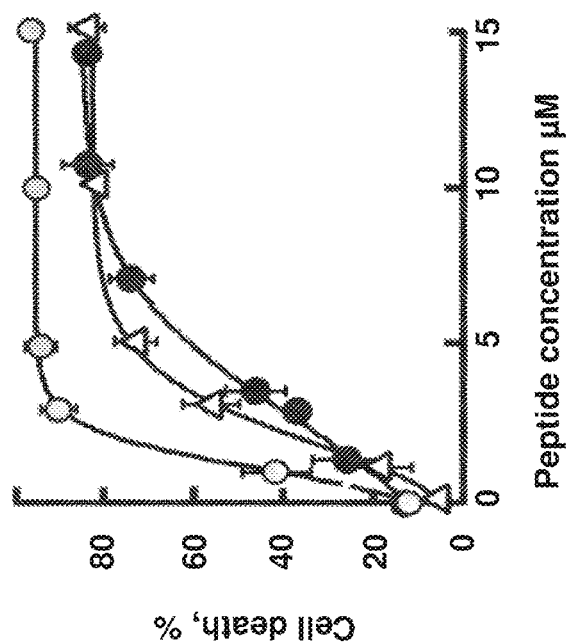
FIG. 6 shows the percentage of cell death of glioblastoma tumor-derived U-87MG cell line induced by a synthetic peptide comprising a VDAC-1 derived peptide LP4 (Tf-D-LP4; (○)); a synthetic peptide comprising a portion of VDAC-1 N-terminal sequence (D-AN-Ter-Antp; (●)) and Rretro-Tf-D-LP4; (Δ)).

Human primary glioblastoma tumor-derived cell lines (U-87MG), at $6 \times 10^5$ cells per ml were incubated in a serum-free medium with the examined peptide at several concentrations for 6 h at 37° C. in the presence of 5% $CO_2$. Peptides used in this experiment were Tf-D-LP4, Retro-Tf-D-LP4 and additional peptide derived from VDAC1, designated D-AN-Ter-Antp, comprising the amino acids sequence D-Arg-D-Asp-D-Val-D-Phe-D-Thr-D-Lys-D-Gly-D-Tyr-D-Gly-D-Phe-D-Gly-D-Leu-D-Arg-D-Gln-D-Ile-D-Lys-D-Ile-D-Trp-D-Phe-D-Gln-D-Asn-D-Arg-D-Arg-D-Met-D-Lys-D-Trp-D-Lys-D-Lys (SEQ ID NO:18). The cells were then trypsinized, centrifuged (1500×g, 5 min), washed with PBS and analyzed for cell death using PI staining and flow cytometer (Beckton-Dickinson, San Jose, Calif.) and BD CellQuest Pro software. As shown in FIG. 6, both Tf-D-LP4 and Retro-Tf-D-LP4 peptides induced similar massive cell death with $EC_{50}$ of 1.5 μM and $EC_{50}$ of 2.2 μM, respectively.

Example 7: Cell Death Induction of Cancer Stem Cells and Cancerous Vs. Non-Cancerous Cell Lines The ability of the retro inverse peptide Retro-Tf-D-LP4 to induce apoptosis in non-cancerous cells compared to cancer cells was tested to establish the cancer specificity of the peptide. U-87MG and MDCK (Madin-Darby Canine Kidney epithelial cells from the kidney tissue of an adult female cocker spaniel) were incubated in a serum-free medium for 6 h with the retro-inverso peptide (Retro-Tf-D-LP4) at several concentrations.

Figures 7A, 7B:
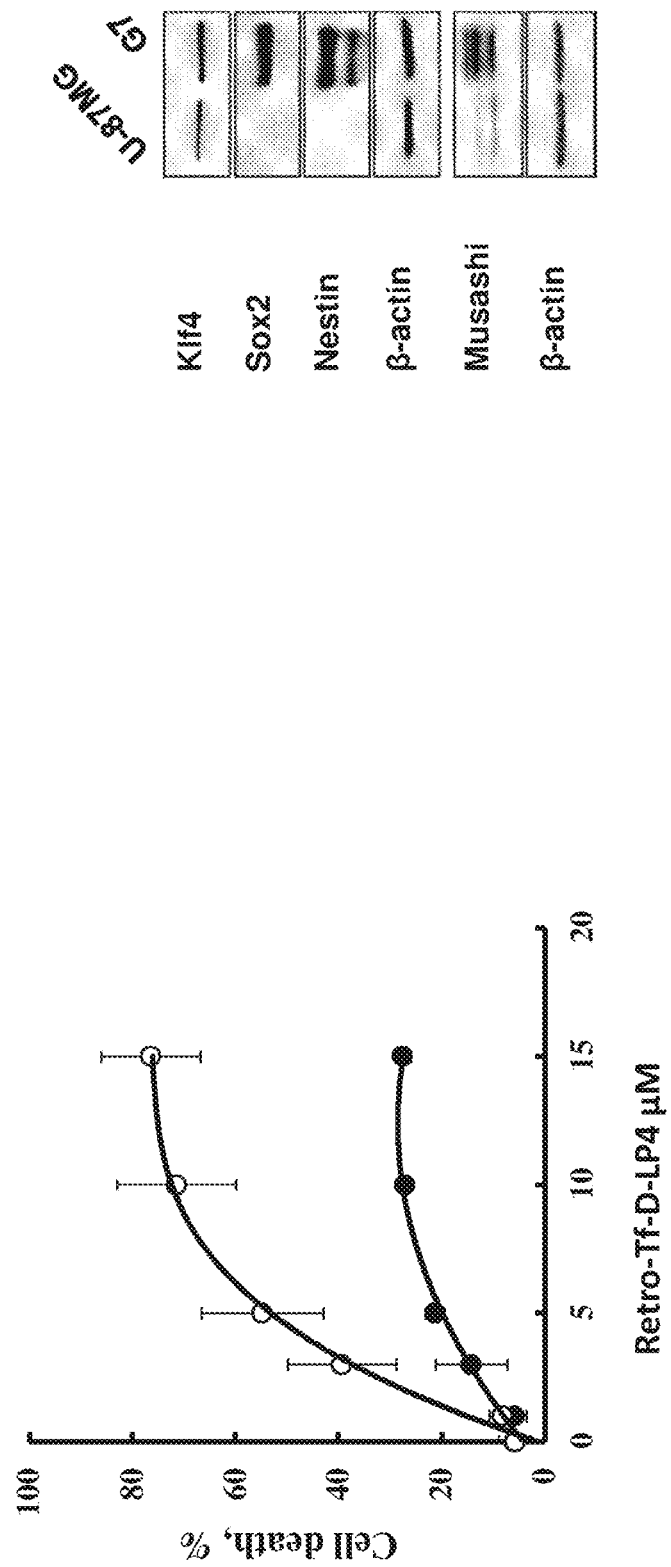
FIG. 7A shows the differential effect of the Retro-Tf-D-LP4 on human glioblastoma cancer cells (U-87MG; (○)) and on non-cancerous MDCK cells (●).
FIG. 7B shows immunoblot analysis of stem cells markers, Klf4, Sox2, Musashi and Nestin expression in U-87MG and G7 stem cells cell lines, using specific antibodies.

FIG. 7A clearly demonstrates that the retro-inverso peptide (Retro-Tf-D-LP4) distinguishes between cancerous and non-cancerous cells, with specificity to cancerous cells. While 15 μM of the Retro-Tf-D-LP4 peptide induced cell death of about 80% in the cancer cell line, same concentration of the peptide induced cell death of only about 30% in the non-cancerous cell line MDCK.

The Retro-Tf-D-LP4 effect on cancer stem cells was also examined using glioma-derived stem cell (GSC) line G7 derived from a GBM patient (Pollard S M et al. 2009. Cell Stem Cell 4(6):568-580). The G7 GSC cell line was grown using specific glioblastoma stem cell medium, as described previously (Pollard S M et al 2009. Cell Stem Cell. 4(6): 568-580.)

Figure 7C:
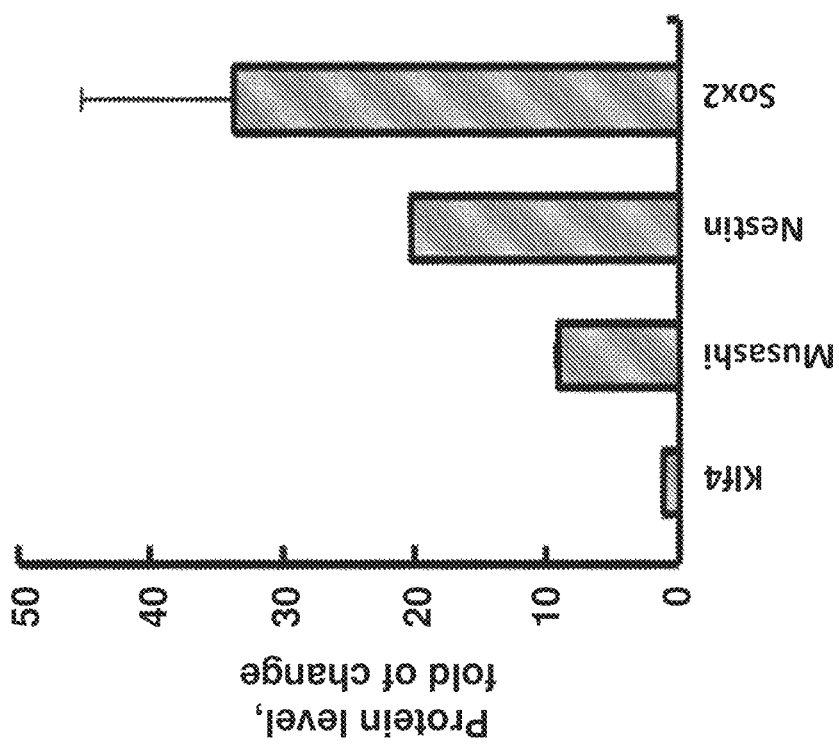
FIG. 7C shows quantitative analysis of the immunoblots presented in FIG. 7B.
Figure 7E:
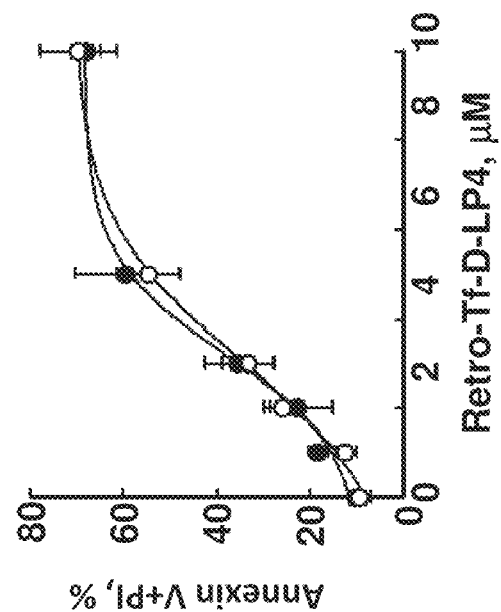
FIG. 7E shows the effect of Retro-Tf-D-LP4 on apoptosis using FITC-Annexin V/PI staining and FACS analysis.
Figure 7D:
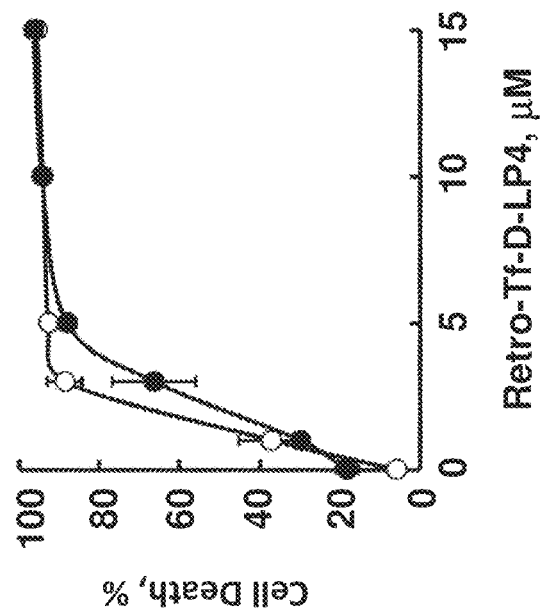
FIG. 7D shows that retro-Tf-D-LP4 effectively induces cell death of G7 stem cells (●) and of U-87MG cells (○) using PI staining and flow cytometry.
Figure 8B:
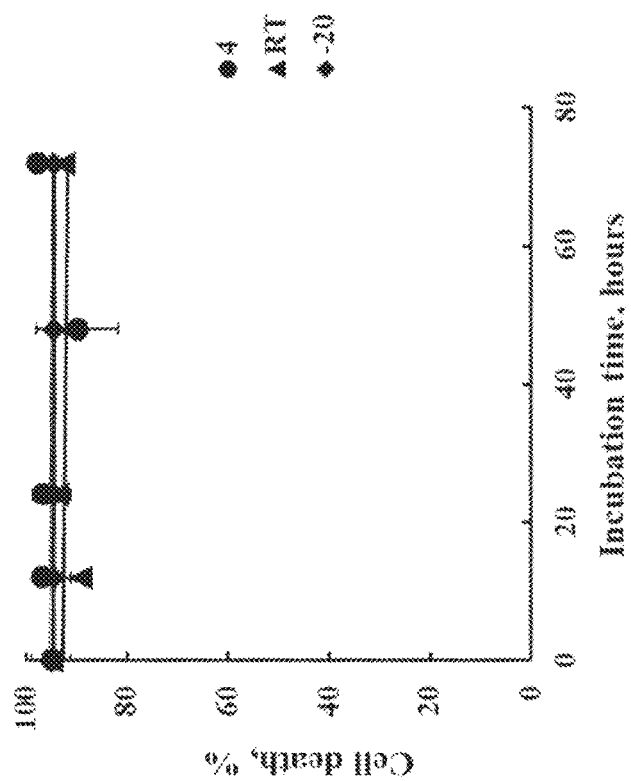
FIG. 8B demonstrates the stability of Retro-Tf-D-LP4. The assay conditions were as described in FIG. 8A above. Retro-Tf-D-LP4 kept its full activity in all temperatures examined, including 4° C. and room temperature.
Figure 8A:
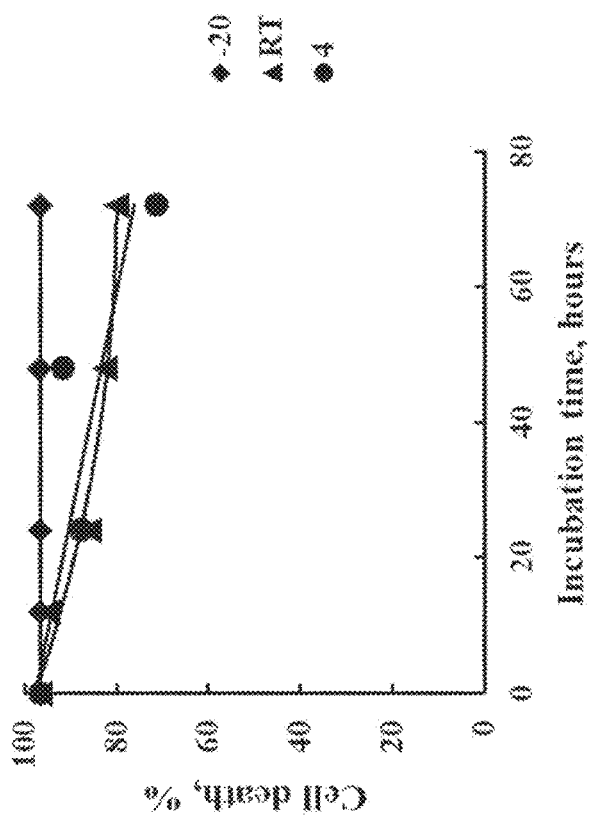
FIG. 8A demonstrates the stability of Tf-D-LP4. The peptide (0.5 mM in 5% DMSO) was incubated at −20° C., 4° C. or 25° C. for the indicated time, and then assayed (at 10 µM) for its capability to induce death of A549 using PI staining and FACS analysis. In untreated cells, cell death was 3%, while with the peptide, cell death was over 90% (n=2). Tf-D-LP4 kept its full activity only when stored at −20° C. and 75% of its activity when stored at 4° C. or 25° C.

The GSC-specific markers, Sox2, Musashi, and Nestin were highly expressed in G7, as compared to U-87MG cells, containing about 1% GSCs, thus confirming the stemness of the cells (FIG. 7B, 7C). Klf4 was expressed in both cell lines with its level in G7 slightly higher. The induction of cell death on the G7 stem cells by the Retro-Tf-D-LP4 peptide was similar to the cell death induction on the U-87MG cell line (FIG. 7D). The concentrations for inducing 50% cell death ($EC_{50}$, n=3) were 1.5±0.3 and 2.5±0.3 μM for U-87MG and G7 cells, respectively. Similar results were obtained when apoptosis was assayed using annexinV/PI staining and FACS analysis (FIG. 7E).

The results thus clearly indicate that GSCs are sensitive to the retro-inverso analogue of the VDAC1-derived peptide.

Example 8: Solubility and Stability of Retro-Tf-D-LP4

The solubility of synthetic peptides comprising VDAC-derived peptides, the control Tf-D-LP4 and the retro-inverso peptide Retro Tf-D-LP4 was evaluated as to assess the peptide compatibility for intravenous administration to animals, in in vivo experiments and treatments. Peptides were dissolved as described hereinabove. Concentration examined was 4 mM; solvent used was DDW/10% DMSO/150 mM NaCl (NaCl added later at a final concentration of 150 mM) as a common physiologically compatible solution for drug administration.

The molecular weight of Tf-D-LP=4111.67 g/mol. Accordingly 1.4 mg peptide (Tf-D-LP4 or Retro-Tf-D-LP4) were weighed using analytical scale. 8.5 μl DMSO 100% were added to the peptide to form a concentration of 40 mM, and the solution was incubated in a water bath at 37° C. for 15 min until the solution became clear. The solution obtained was diluted by about 10-fold with DDW reaching a final concentration of 4.4 mM (11.1% DMSO), incubated in a water bath at 37° C. for 15 min, and then incubated overnight at 4° C. After incubation, the solution was centrifuged for 5 min. at 15,000×g. The supernatant was transferred to a fresh Lobind Eppendorf tube and NaCl was added to a final concentration of 0.15M. The resulted solution was incubated in water bath at 37° C. for 15 min, centrifuged for 5 min. at 15,000×g and the supernatant was transferred to a fresh Lobind Eppendorf tube. Peptide concentration in each step was analyzed.

Determining Peptide Concentration

Peptide concentration was determined from the absorbance at 280 nm following its denaturation and using the following calculation:

Weight/volume (mg/ml) concentration was calculated according to the equation:

$$mg\ peptide/ml = (AU \times DF \times Mw)/[(TrypW\# \times 5560) + (TyrY\# \times 1200)]:$$

Figure 9:
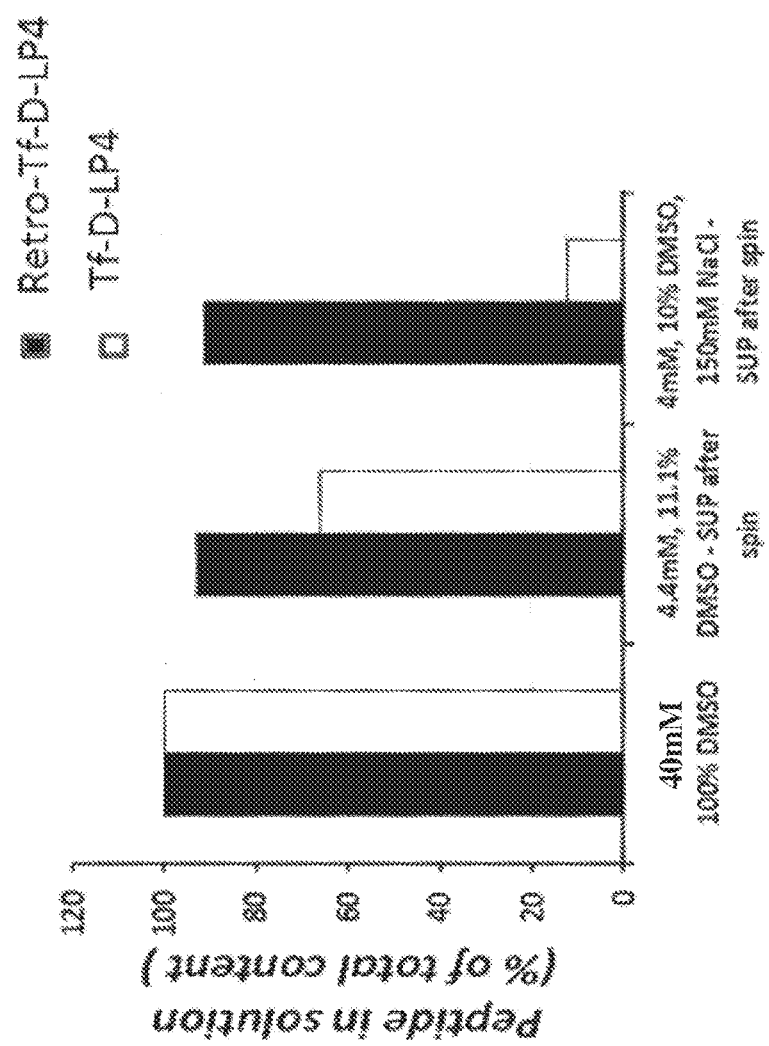
FIG. 9 demonstrates the higher solubility of Retro-Tf-D-LP4 relative to Tf-D-LP4. The peptides were dissolved in 100% DMSO then diluted by about 10-fold to reduce DMSO to 10-11% and the peptide to 4.4 or 4 mM, and the amount of the soluble peptide was analyzed in the supernatant (SUP) following centrifugation to remove insoluble peptide. The higher solubility of the Retro-Tf-D-LP4 relative to Tf-D-LP4 is shown.

AU—peptide absorbance measured
DF—dilution factor
Mw—Molecular weight
TrypW #—number of Tryptophan in the peptide sequence
TyrY #—number of Tyrosine in the peptide sequence FIG. 9 presents a comparison between solubility of Tf-D-LP4 (white bars) and of Retro-Tf-D-LP4 (black bars) peptides as percentage of soluble peptide out of the total peptide content as calculated by 280 nm absorbance analysis described hereinabove. As is clearly demonstrated in FIG. 9, most of the Retro-Tf-D-LP4 was dissolved when the DMSO concentration was reduced to 10%, while under this conditions only about 10% of Tf-D-LP4 were dissolved.

Both peptides, Tf-D-LP4 and Retro-Tf-D-LP4, showed high solubility in 100% DMSO. Unexpectedly, at 10% DMSO the retro-inverso Retro-Tf-D-LP4 peptide was shown to be 5-7-fold more soluble compared to Tf-D-LP4.

This feature of the Retro-Tf-D-LP4 is of significant importance, as it enables its formulation for pharmaceutical use.

Example 9: Peptide Encapsulation

Figure 10A:
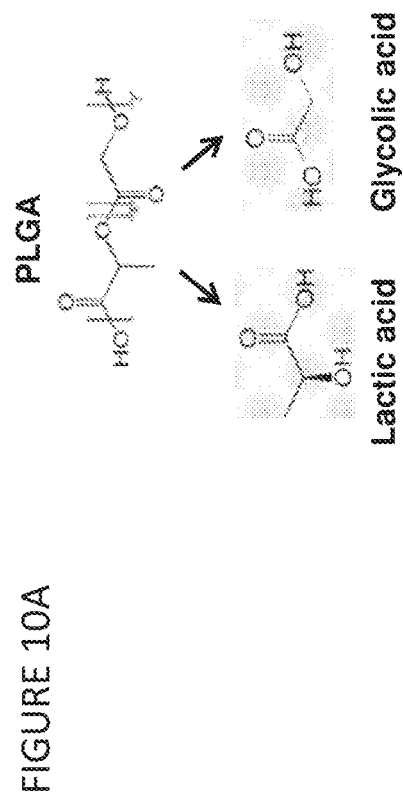
FIG. 10A shows structure of poly lattice-co-glycolide (PLGA) and its degradation products.

One main obstacle in using peptides as therapeutic drugs for treating solid tumors, particularly for treating brain tumors, is delivering the therapeutic peptide to the affected area, and in the case of brain tumors, crossing the blood-brain barrier (BBB). The BBB is highly restrictive and selective, allowing passage of only very small molecules (<600 Da) or peptides that pass by diffusion or via specific transporters. Drugs encapsulated in nanoparticles or conjugated to a sequence that is recognized and imported by cell receptors are able to cross the BBB. Here, we used Retro-Tf-D-LP4 assuming it will cross the BBB via the TfR which is highly expressed in BBB (e.g. Bien-Ly N et al. 2014. J Exp Med. 211(2), 233-244) and using nanoparticles made of poly lattice-co-glycolide (PLGA) (FIG. 10A), allowing controlled release of the cargo.

Figure 10B:
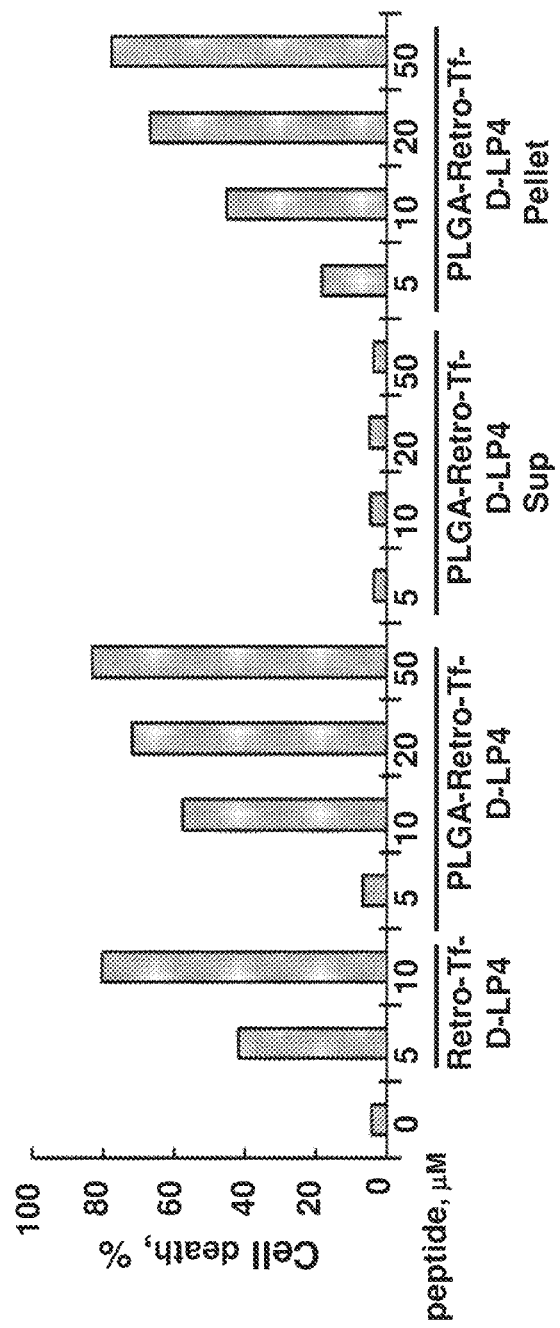
FIG. 10B shows that the peptide Retro-Tf-LP4 was encapsulated in PLGA nano-particles as revealed by cell death induction with the PLGA-encapsulated Retro-Tf-D-LP4 (pellet) and not by the supernatant (sup). Cell death was analyzed by PI staining and FACS analysis.

Retro-Tf-D-LP4-loaded PLGA complexes were prepared by the solvent displacement method with some modifications, as previously reported (Andrieu V et al. 1989. Drug Des Deliv 4, 295-302; Das J et al. 2104. Toxicol Lett 225, 454-466). Twenty milligrams of Retro-Tf-D-LP4 were dissolved in 40 μl of 100% DMSO and then diluted 20-fold with sterile DDW to reach a concentration of 25 mg/ml in a final DMSO concentration of 5%. PLGA (50 mg) was dissolved in acetone (1 ml). Then, 105 μl of peptide were added to the PLGA-acetone solution. The resulting peptide-PLGA-acetone mixture was added drop-wise (0.5 ml/min) into 10 ml of aqueous solution containing 1% PVA (w/v). The mixtures were stirred continuously at room temperature until complete evaporation of the organic solvent. The nanoparticles were centrifuged at 15,000 g (4° C. for 20 min) and the pellet was re-suspended in sterile DDW and washed two times. The resulting pellet was mixed with HBSS solution and used for i.v. injection to mice. To demonstrate that the peptide is encapsulated within the PLGA nanoparticles and active, the particles were centrifuged, and the cell death inducing activity of the resulting supernatant and the re-suspended nanoparticles was analyzed (FIG. 10B). The results clearly indicated that the peptide was encapsulated in the PLGA nano-particles and induced cell death in U-87MG cells.

Example 10: In Vivo Effect of Retro-Tf-D-LP4 on Tumor Cell Death

The in vivo effect of Retro-Tf-D-LP4 was examined using brain orthotopic tumor model. Orthotopic models currently offer the best way to study the characteristics of a tumor in the context of a live animal, particularly at sites with unique physiological and architectural qualities, such as the brain. These models allow for assessment of features such as metabolism, drug delivery across BBB, and toxicity. To better mimic the clinical situation of Glioblastoma multi-forme (GBM), intracranial-orthotopic xenografts (Pierce A M and Keating A K. 2014. J Vis Exp. 91, 52017) was used to examine the Retro-Tf-D-LP4 peptide effectiveness in inhibiting tumor growth.

Figure 11A:
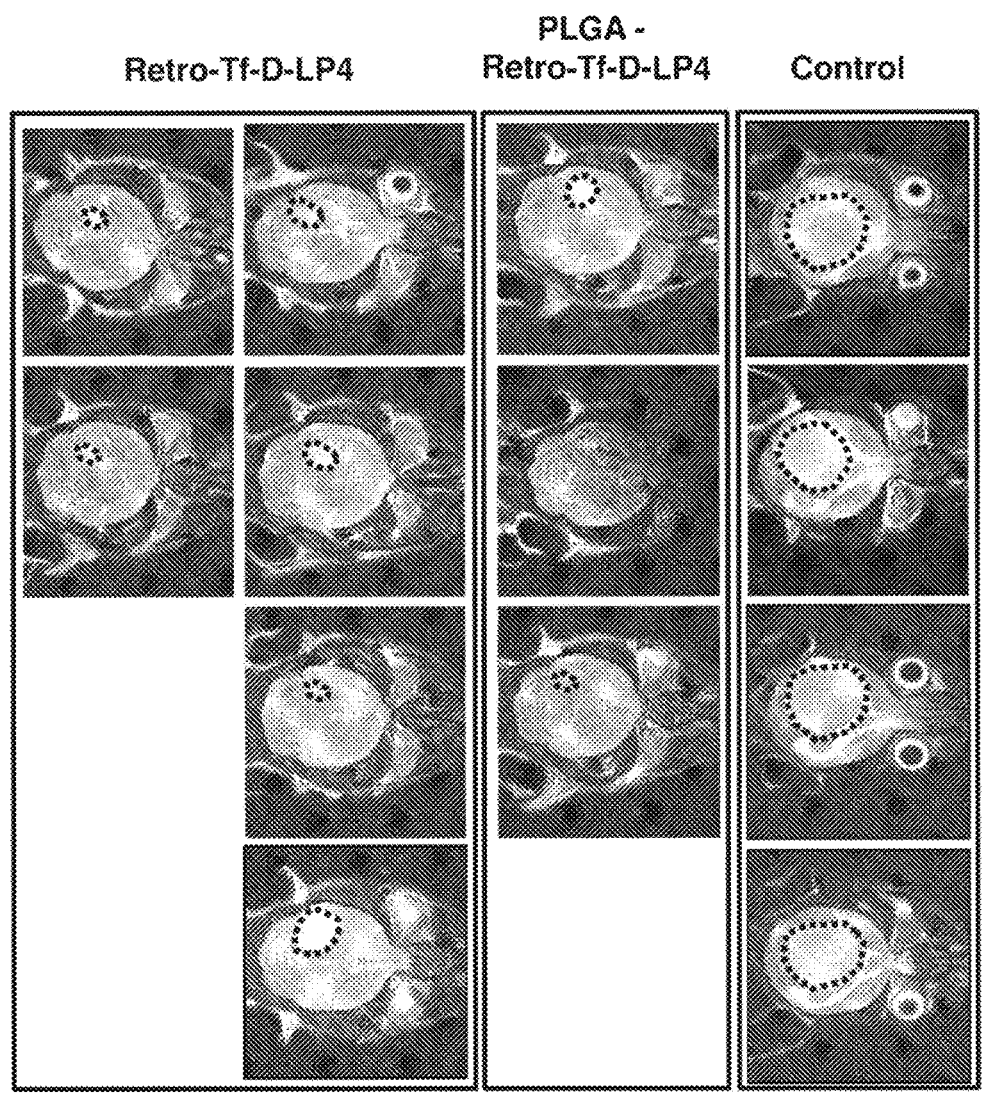
FIG. 11A shows an Mill imaging of brains of mice 32 days after engrafting with U-87MG cells.
Figures 11B, 11C:
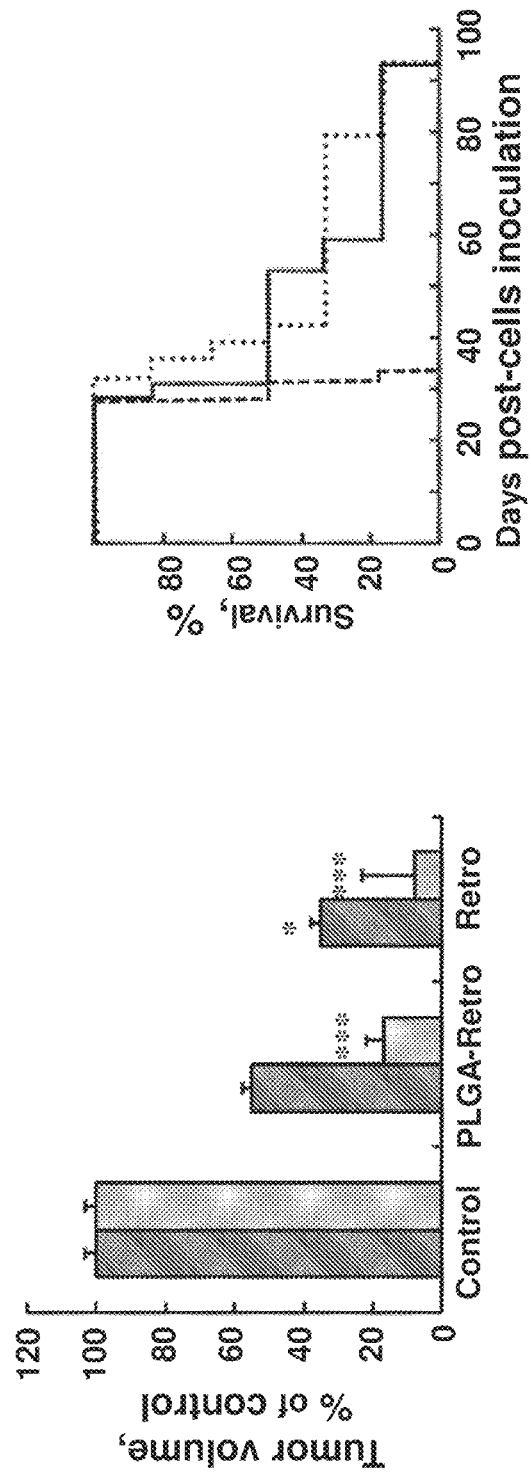
FIG. 11B presents the calculated tumor volume after 25 (dark grey columns) and 32 (light grey columns) days of cell engraftment. Results=mean±SE (n=6) (*p<0.05, ***p<0.001).
FIG. 11C presents Kaplan-Meier survival curves showing statistically significant differences in survival curves between the PBS/DMSO and Retro-Tf-D-LP4 treated mice. Cumulative Kaplan-Meier survival curves of control mice (dotted line), Retro-Tf-D-LP4 peptide (10 mg/kg) encapsulated in PLGA nanoparticles (black line) or Retro-Tf-D-LP4 peptide (10 mg/Kg, broken line).

U-87MG cells ($8 \times 10^4$) were engrafted into nude mice brains, and mice were treated intravenously (i.v.) with DMSO (1.05%) in PBS; Retro-Tf-D-LP4 (10 mg/Kg) encapsulated in PLGA nanoparticles; or free Retro-Tf-D-LP4 peptide (10 mg/Kg). 25 and 32 days later, tumor growth was monitored by MRI (FIG. 11A). Decreases of 80% and 90% in orthotopic xenograft tumor volume were obtained when mice were treated intravenously with free Retro-Tf-D-LP4 peptide (10 mg/Kg) 25 and 32 days post-treatment start (FIG. 11B). Similarly, treatment with PLGA-encapsulated (10 mg/Kg) Retro-Tf-D-LP4, showed decreases of 45% and 65% in orthotopic xenograft tumor volume 25 and 32 days post-treatment start, respectively (FIG. 11B).

Analysis using Kaplan-Meier survival curves revealed statistically significant differences in survival between the PBS/DMSO and free- or PLGA-encapsulated Retro-Tf-D-LP4-treated mice (FIG. 11C). Peptide treatment prolonged the survival of 40 and 50% of the mice treated with the free- or PLGA-encapsulated Retro-Tf-D-LP4, respectively, over the 35 days survival observed for untreated mice.

The results clearly demonstrate that both free- and PLGA-encapsulated Retro-Tf-D-LP4 preparations, administrated intravenously, can cross the BBB, reach the tumor cell and effectively induce tumor cell death, with free Retro-Tf-D-LP4 being more effective both in reducing tumor size and in mice survival.

Example 11: Inhibition of DEN-Induced Cancer by Retro-Tf-D-LP4

The genotoxic drug diethylnitrosamine (DEN) is the most widely used chemical for induction of liver cancer in mice. DEN undergoes metabolic activation in hepatocytes by enzymes of the cytochrome P450 family and acts as a complete carcinogen, if injected into male mice younger than 2 weeks, when hepatocytes are still actively proliferating (Bakiri L and Wagner F. 2013. Mol Oncol 7, 206-223). DEN-induced hepatocellular carcinoma (HCC) is a progressive process with tumors visible in week 30-32 post DEN treatment.

DEN-induced HCC in mice was performed as described above (summarized in FIG. 12A). Livers were imaged by MRI (FIG. 12B, 12C). Livers from the scarified mice were photographed for macroscopic pathological observation (FIG. 12D). In the untreated, control group mice livers showed high number of tumor nodules (FIG. 12B, 12D), whereas in mice treated with the peptide no tumor nodules were observed (FIG. 12 C, 12D). In the control group livers were big in size and weight comparing to livers from mice treated with the Retro-Tf-D-LP4 peptide (FIG. 12E). These results show that the peptide inhibited tumor development.

Example 12: Inhibition of Steatosis by Retro-Tf-D-LP4

Morphological Changes

Figure 13A:
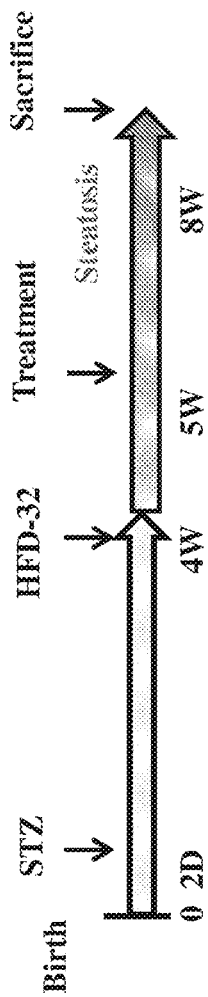
FIG. 13A is a schematic presentation of the course of steatosis development induced by high fat diet (HFD) and of the initiation of Retro-Tf-D-LP4 peptide treatment.
Figure 13B:
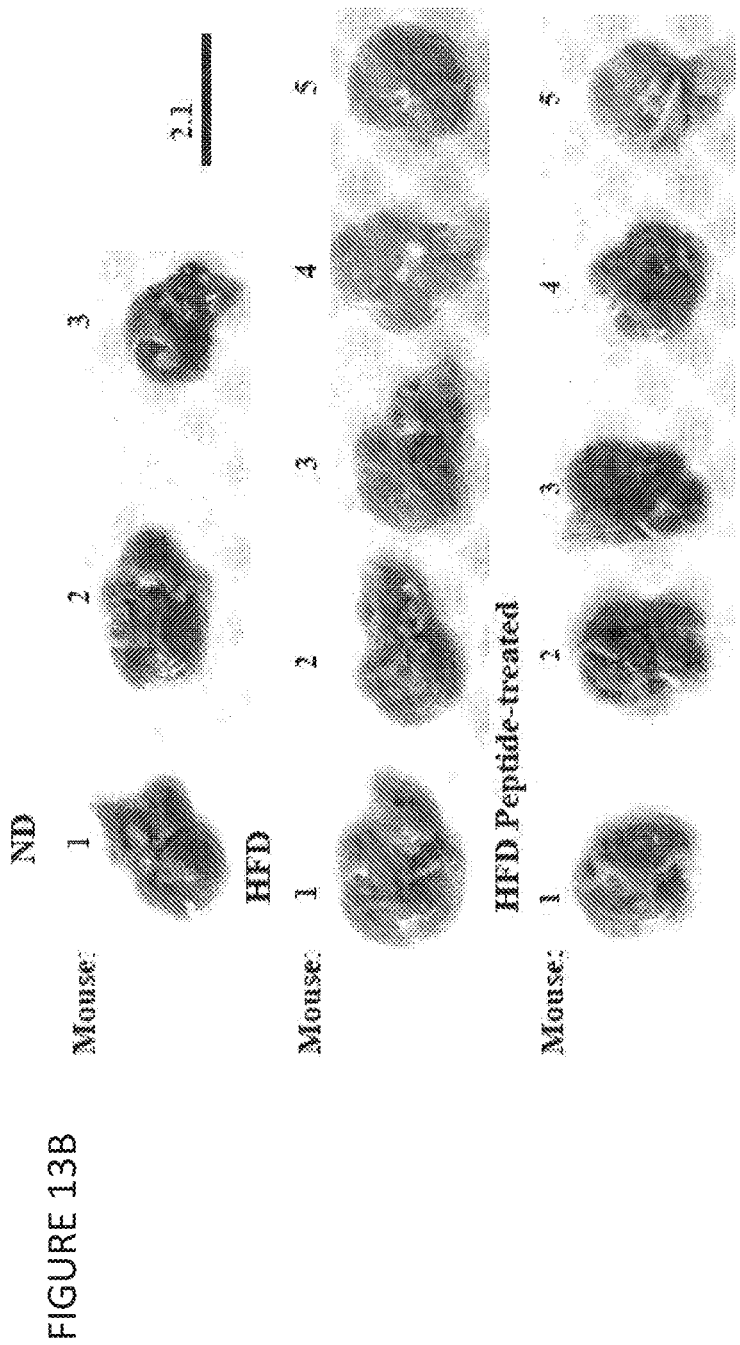
FIG. 13B shows photographs of livers removed after mice were scarified at the end of week 9.
Figures 13C, 14:
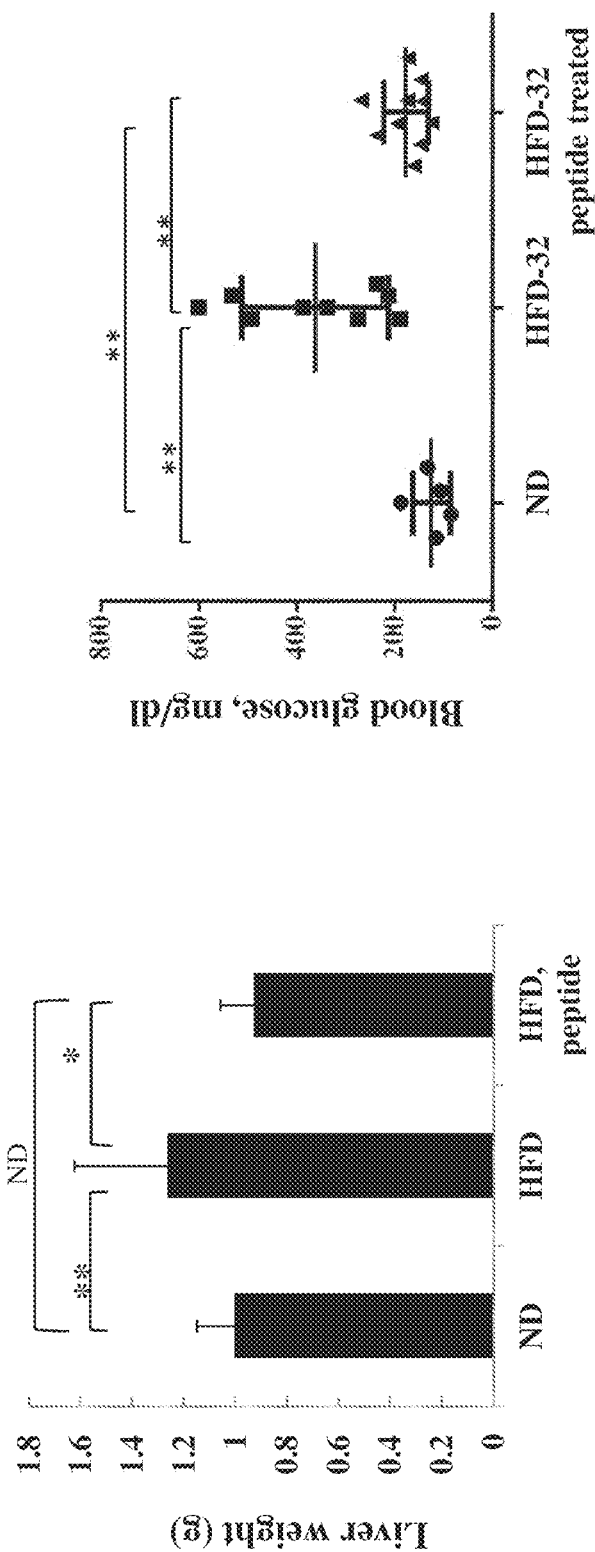
FIG. 13C shows the weight of the livers presented in FIG. 13B (ND: chow (normal) diet). Results=mean±SEM (n=5) (p:*, 0.05; **≤0.005).
FIG. 14 shows the blood glucose levels in mice that received chow diet (ND), mice that received HFP-32 diet and mice that received HFD-32 and treated with the Retro-Tf-D-LP4 peptide. Results=mean±SEM (n=5), (p: **≤0.003).

To study the effect of the peptide on steatosis, mice were subjected to regular chow diet (control) or to high fat diet (HFD-32) for 5 weeks (mice 4-9 weeks old), where during the last 2 weeks the mice were treated with DMSO 2% in HBSS or with Retro-Tf-D-LP4 (10 mg/kg). The course of the study was as schematically represented in FIG. 13A. At the end of week 9, mice were sacrificed, livers were photographed (FIG. 13B) and weighed (FIG. 13C) and then fixed or frozen for further processing for histopathological analyses. Livers from mice that received HFD-32 showed yellowish color in comparison to livers of mice that received regular (chow)-fed or of mice treated with the Retro-Tf-D-LP4 peptide (FIG. 13B). The weight of the livers from mice fed with HFD-32 increased by about 30% in comparison to the weight of livers of regular (chow)-fed mice, while this increase was attenuated in the HFD-32 mice treated with the retro-inverso peptide (FIG. 13C). These results point to increased fat and liquid accumulation (inflammation) in the liver tissue of HFD-32 mice, which can be treated by Retr-Tf-D-LP4.

Retro-Tf-D-LP4 Decreased the Blood Glucose Level in HFD-STAM Mice

In agreement with previous findings, blood glucose levels were highly increased in mice receiving the HFD-32 diet, from about 150 mg/dL in mice fed with regular (chow) food up to 450 mg/dL in mice fed with HFD-32 (FIG. 14). This increase was suppressed in mice treated with Retro-Tf-D-LP4, showing blood glucose levels comparable to those of mice fed with regular food.

Liver Histopathological Changes

Morphological changes were evaluated on fixed, paraffin-embedded liver sections, using H&E staining. Representative H&E stained sections of liver tissue from HFD-32-fed mice display signs of steatosis characterized by displayed fat droplet accumulations in hepatocytes, by scattered inflammatory cell infiltrates and by fibrosis (FIGS. 15, 16).

Figure 15A:
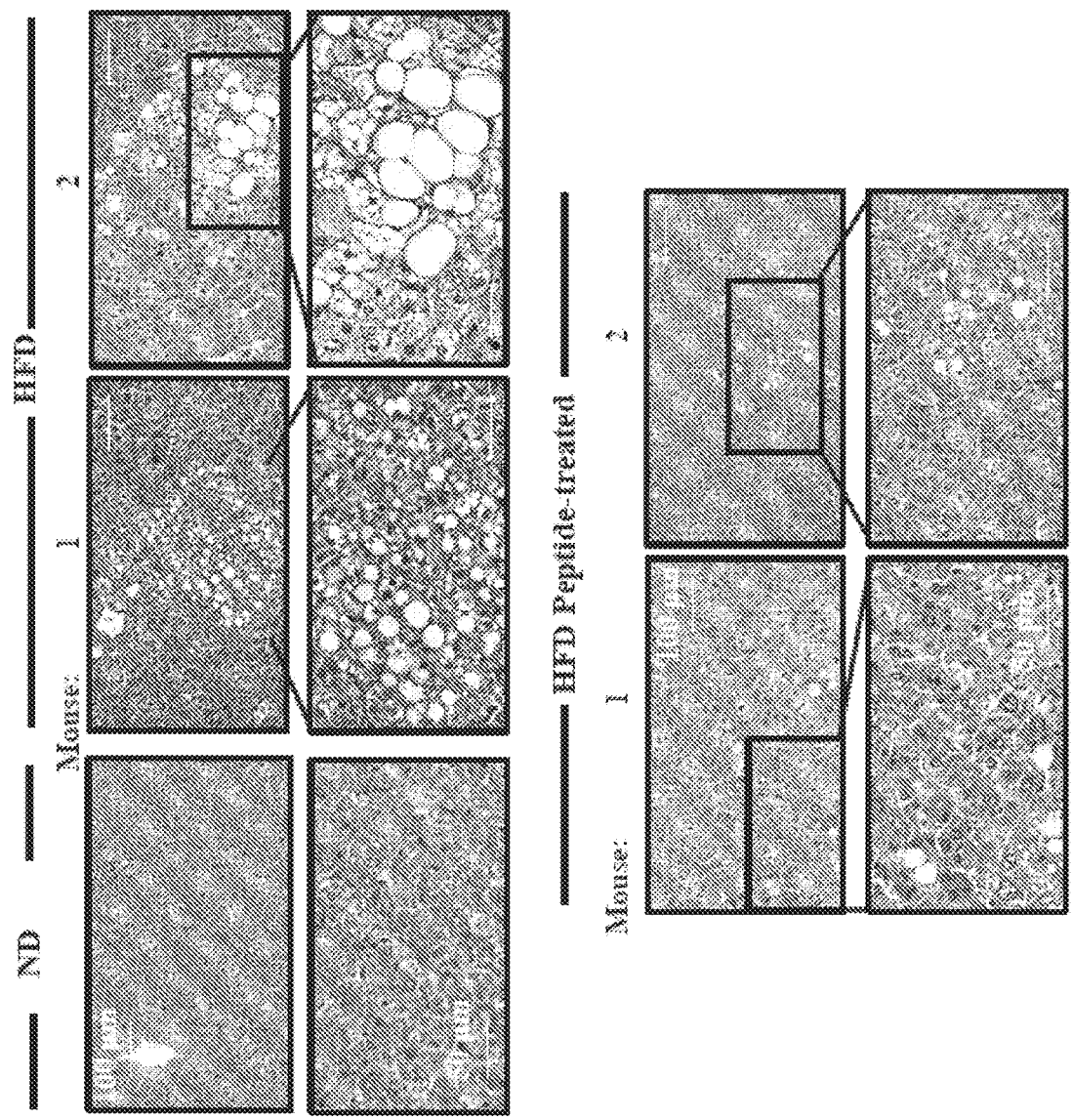
FIG. 15A shows representative H&E staining of liver sections taken from mice that received chow diet (ND), mice receiving HFD and treated with 0.9% DMSO in HBSS buffer i.v. or mice receiving HFD and treated with Retro- Tf-D-LP4 (10 mg/Kg, 0.9% DMSO) i.v. Steatosis developed in HFD—was prevented upon Retro-Tf-D-LP4 treatment.

Livers from HFD-32-fed mice displayed fat droplet accumulations. In contrast, livers from peptide-treated mice showed clear reduction both in the size and the number of fat droplets (FIG. 15A).

Figure 15B:
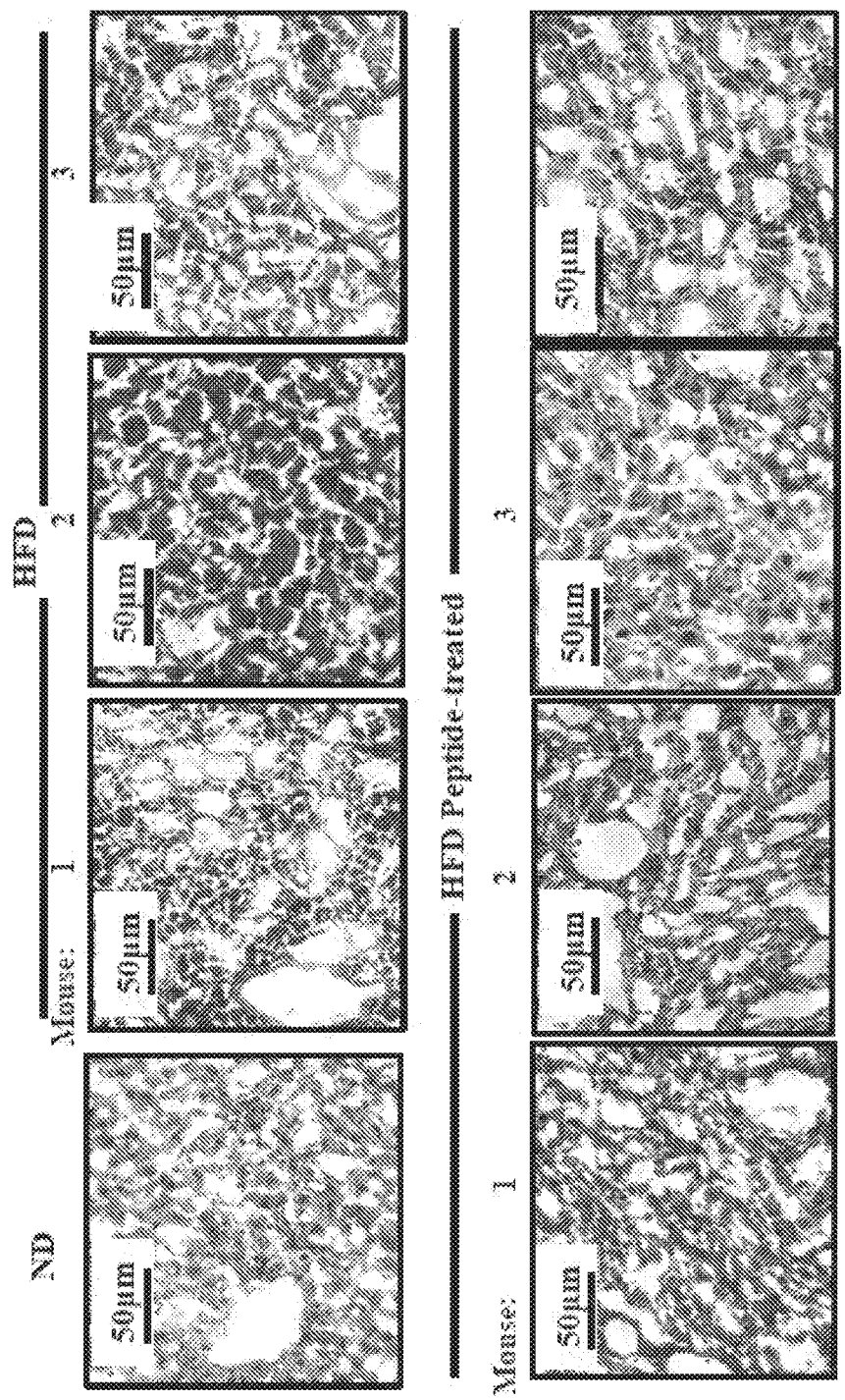
FIG. 15B shows representative Oil red staining of the liver sections described in FIG. 15A. Steatosis developed in HFD—was prevented upon Retro-Tf-D-LP4 treatment.

To better visualize fat droplets, liver sections were subjected to Oil-red staining. Liver sections from three HFD-32-fed mice showed high red staining of fat droplets, occupying the liver, while no such staining was observed in liver sections from regular (chow)-food-fed mice or HFD-32-fed mice treated with the peptide (FIG. 15B).

Figure 16A:
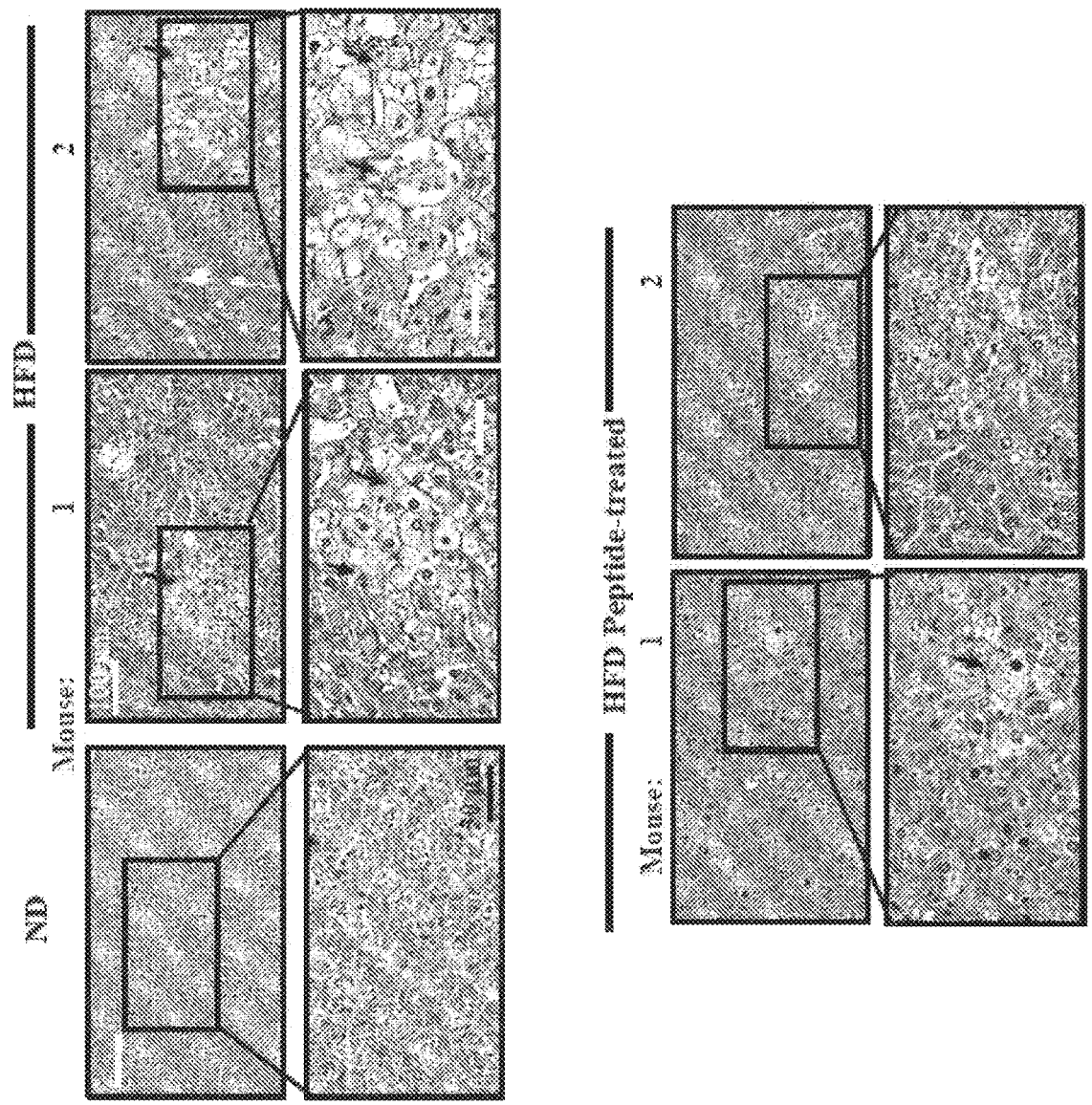
FIG. 16A shows representative H&E staining showing the positive effect of Retro-Tf-D-LP4 i.v. treatment, resulting in inhibition of hepatocyte ballooning associated with steatosis.

Another characteristic of steatosis is the apparent ballooned hepatocytes cell morphology, typically being two to three times the size of adjacent hepatocytes and characterized by a wispy cleared cytoplasm on H&E stained sections. Ballooning degeneration of hepatocytes are associated with hepatocyte cell death (Yip W W and Burt A D. 2006. Semin Diagn Pathol 23, 149-160). Livers from HFD-32-fed mice displayed accumulation of ballooned cells (FIG. 16A). In contrast, livers from mice fed with regular (ND, chow) food show no ballooning cells and mice fed with HFD-32 and treated with the peptide showed highly reduced ballooning cells (FIG. 16A).

Figure 16B:
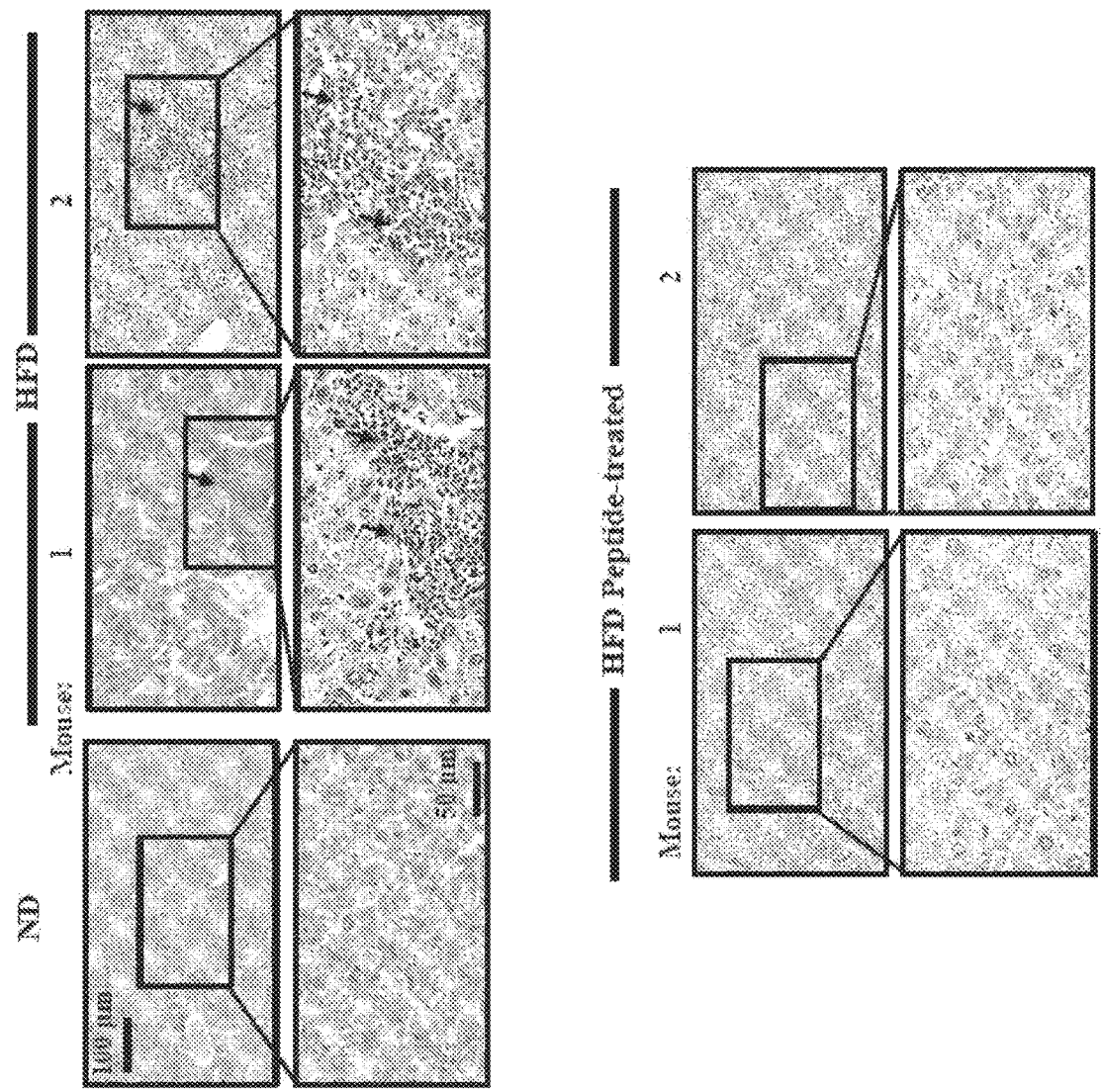
FIG. 16B shows representative H&E staining showing the positive effect of Retro-Tf-D-LP4 i.v. treatment, resulting in inhibition of inflammation (arrows) associated with steatosis.
Figure 16C:
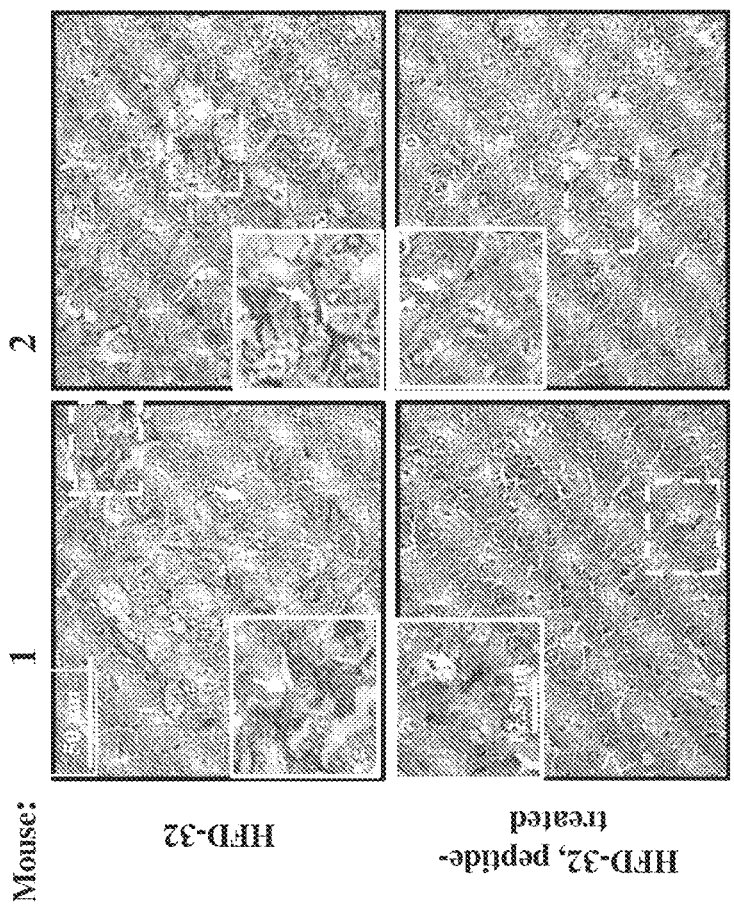
FIG. 16C shows Sirius red staining for fibrosis (arrows). Fibrosis was visible in livers of mice that received HFD-32 but not in mice that received HFD-32 and treated with Retro-Tf-D-LP4 (10 mg/Kg) mice or in mice that received how diet (ND).

The hepatocyte ballooning phenomenon is associated with inflammation (steatohepatitis) (Liangpunsakul S and Chalasani N. 2003. Curr Treat Options Gastroenterol 6, 455-463). Indeed, H&E staining showed inflammatory districts in livers of mice fed with HFD-32. In the histological sections derived from peptide-treated mice, highly reduced inflammation was observed in the liver tissue sections (FIG. 16B). Fibrosis was visible in livers of mice fed with HFD-32 following staining with Sirius red staining, but highly decreased in mice treated with the retro-inverso Retro-Tf-D-LP4 peptide (FIG. 16C).

Retro Tf-D-LP4 Peptide Inhibits/Reverse NASH

Histologically, NASH is characterized by macrovesicular steatosis, with the fat globules vary in size from very small to nearly filling the hepatocyte and by ballooning degeneration of hepatocytes with or without Mallory bodies, with fibrosis (Kleiner D et al. 2005. Hepatology 41, 1313-1321).

Figure 17A:
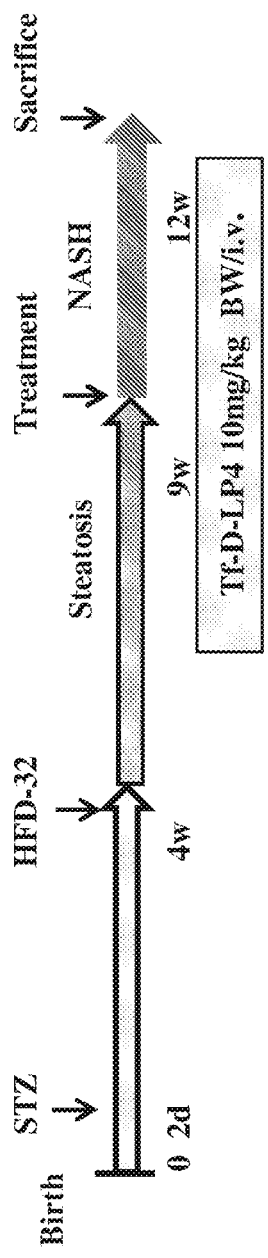
FIG. 17A shows schematic presentation of NASH development post-steatosis-induced by HFD-32 diet and the starting point of peptide treatment.
Figure 17B:
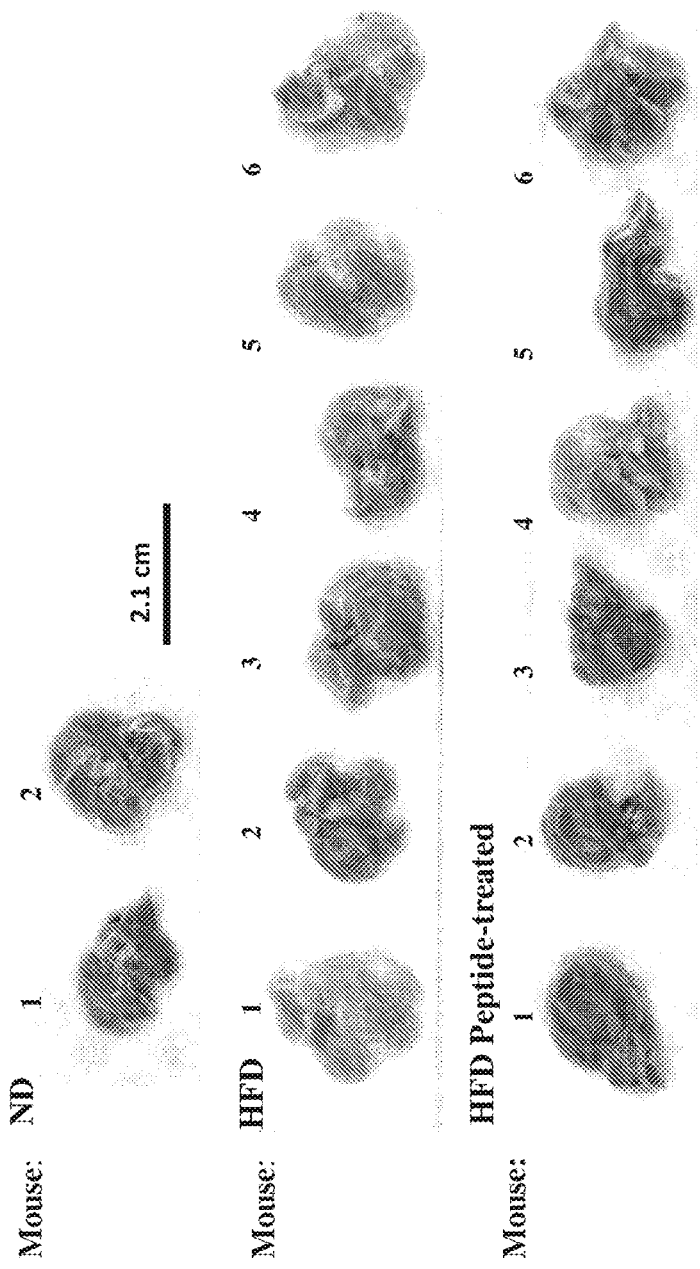
FIG. 17B shows photographs of livers removed after mice were scarified at the end of week 12.
Figure 17C:
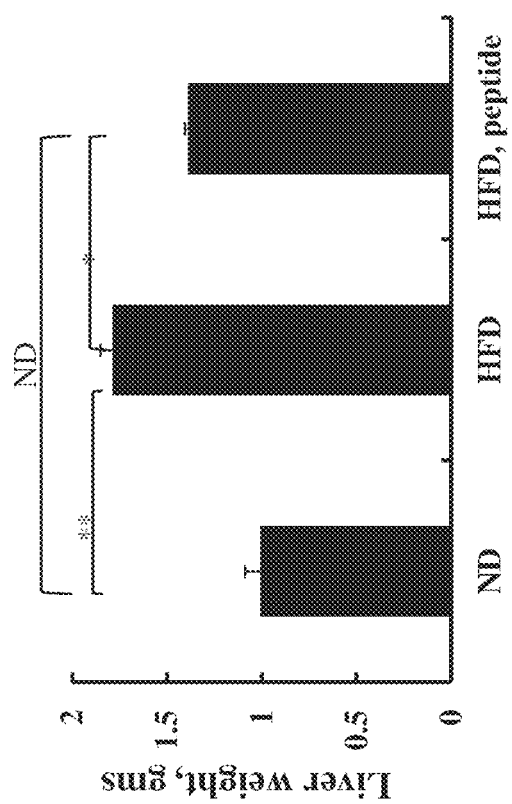
FIG. 17C shows the weight of the livers presented in FIG. 17B (p: *≤0.05, **≤0.01).

In the present study, mice were subjected to regular chow diet (control) or to HFD-32 fed for 8 weeks (mice 4-12 weeks old), where during the last 3 weeks mice were treated with DMSO 0.9% in HBSS, or with Retro-Tf-D-LP4 (10 mg/kg) (FIG. 17A). At the end of week 12, mice were sacrificed, livers photographed (FIG. 17B), weighed (FIG. 17C) and then fixed or frozen for further processing for histopathological, immunoblotting, or qPCR analyses. Livers from mice receiving the HFD-32 diet looked yellow in comparison to mice receiving regular (chow)-fed or mice receiving HFD-32 diet treated with the Retro-Tf-D-LP4 peptide (FIG. 17B). The weight of the livers from the HFD-32-fed mice increased by about 1.8 fold in comparison to livers of regular (chow)-fed (ND) mice, while this increase was only 1.4 fold in mice fed with HFD-32 and treated with the retro-inverso peptide (FIG. 17C).

Figure 17D:
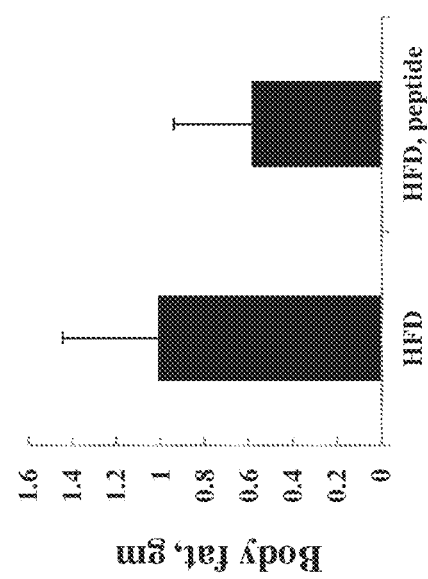
FIG. 17D shows body fat weight in: Epididymal fat (epididymis), mesenteric (mesentay) fat isolated from mice that received HFD-32 and from mice that received HFD-32 and treated with the Retro-Tf-D-LP4 peptide (n=5).

Fat may be accumulated in internal organs, as liver or body, mostly in the abdominal cavity (Visceral fat or abdominal fat). Thus the epididymal fat (epididymis), and mesenteric fat (mesentay) were collected from HFD-32-fed mice and from HFD-32-fed mice treated with the Retro-Tf-D-LP4 peptide. The later showed about 40% less fate in compression to untreated mice (FIG. 17D).

Figure 18A:
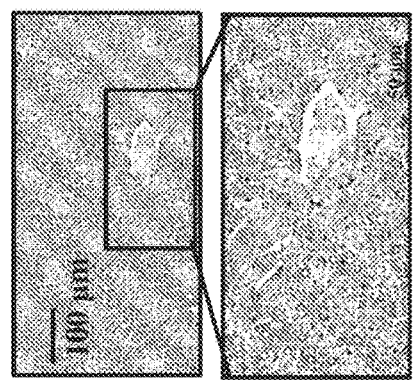
FIG. 18A shows representative H&E staining of liver sections from mice that received chow (ND).
Figure 18B:
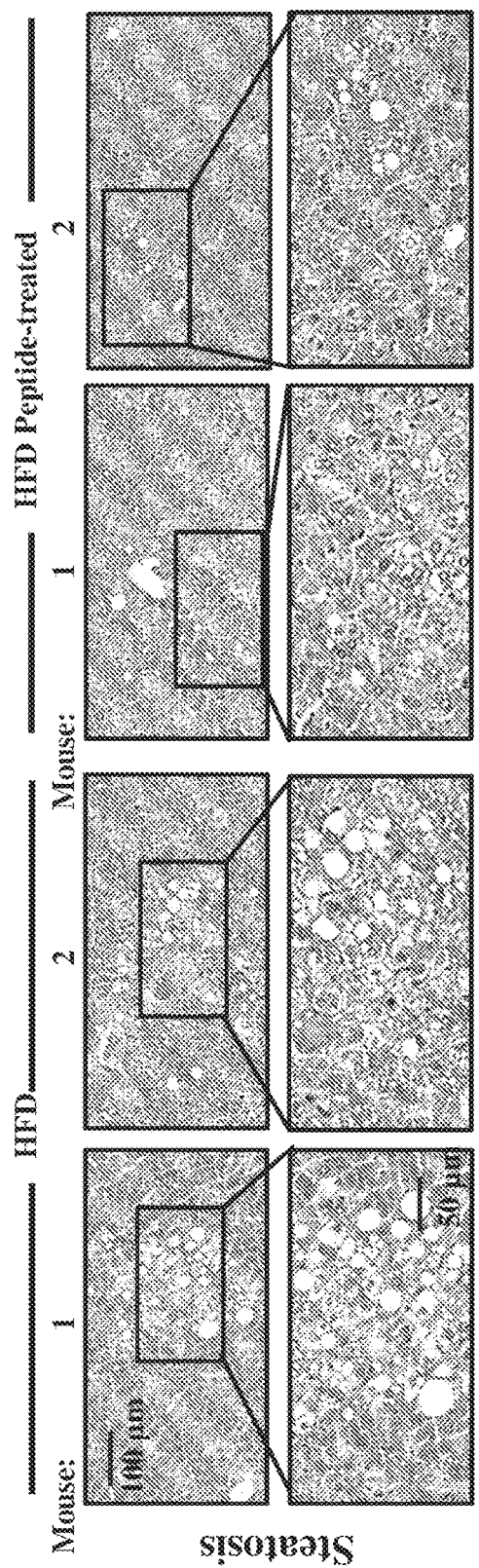
FIG. 18B shows representative H&E staining of liver sections from mice affected with NASH showing steatosis.
Figure 18C:
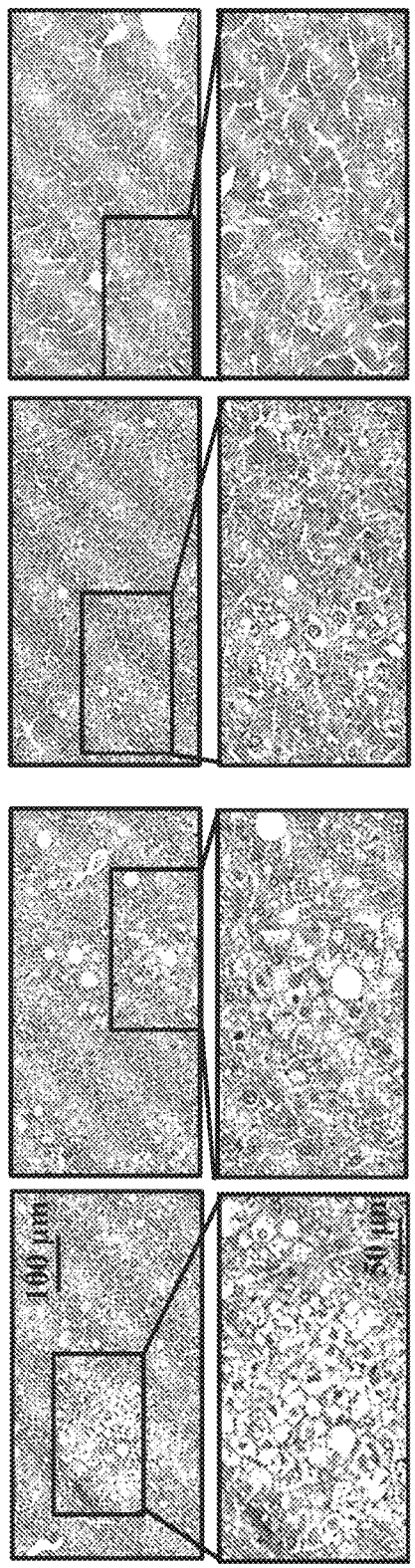
FIG. 18C shows representative H&E staining of liver sections from mice affected with NASH showing ballooning.
Figure 18D:
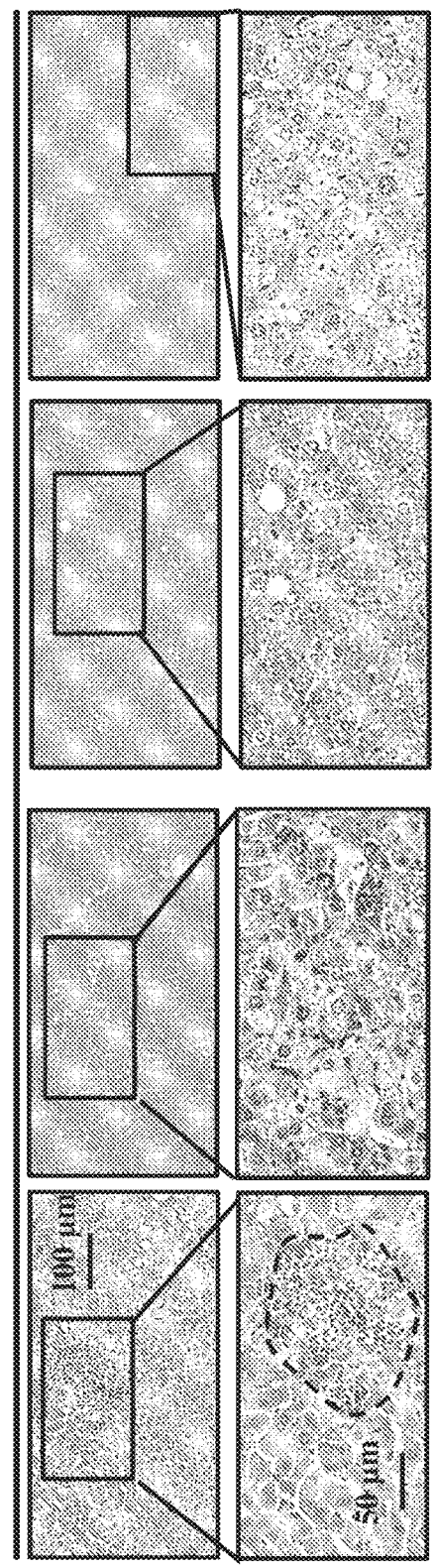
FIG. 18D shows representative H&E staining of liver sections from mice affected with NASH showing inflammation (circled).

Representative H&E stained sections of NASH liver tissues from HFD-32-fed mice showed, as shown above for steatosis, fat droplet accumulations with macro- and micro-vesicles that are highly decreased in the peptide-treated group (FIG. 18B). In liver sections from HFD-32-fed mice, ballooned hepatocytes morphology (FIG. 18C) and inflammation (FIG. 18D) were clearly observed. In contrast, livers from mice fed with regular (chow) showed no ballooning cells or inflammation signs (FIG. 18A) and HFD-32 fed mice treated with the Retro-Tf-D-LP4 peptide showed almost no signs of ballooning and inflammation (FIG. 18B-D).

Figure 19:
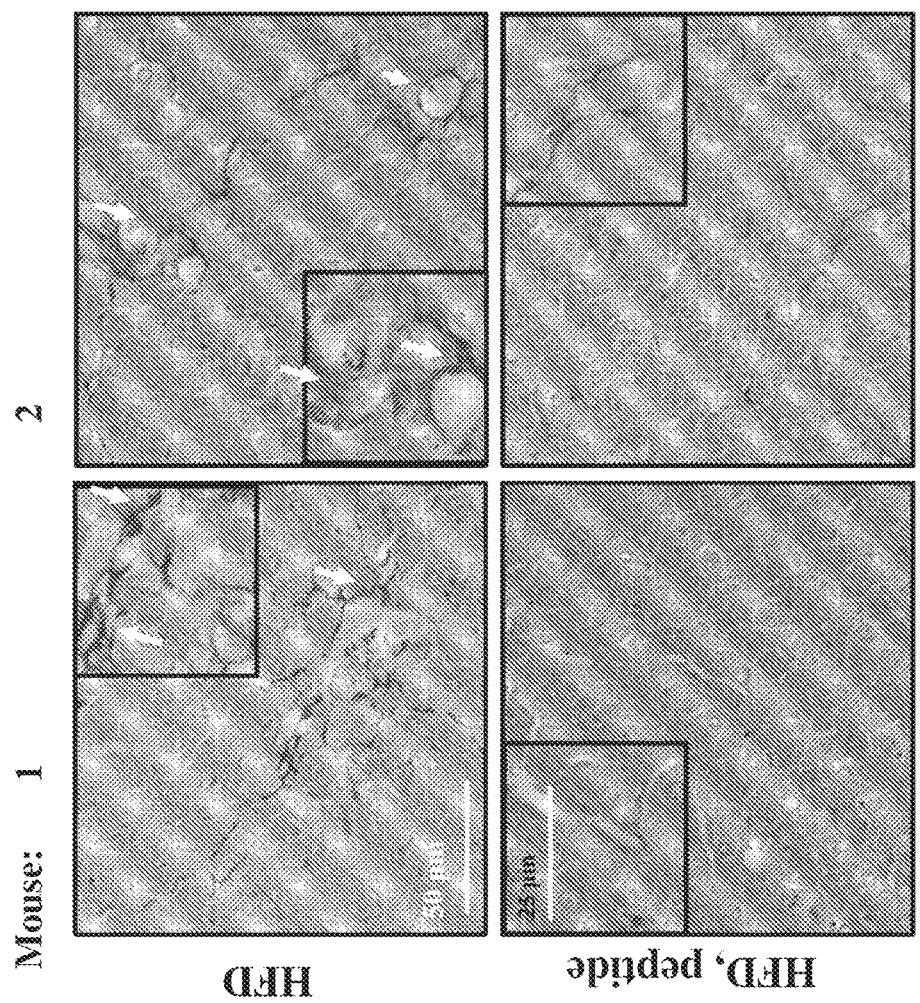
FIG. 19 shows Sirius red staining of mice liver sections from NASH post-steatosis-induced by HFD-32 diet and from mice treated with the Retro-Tf-D-LP4 peptide. Arrows point to the presence of fibrosis (collagen).

Liver fibrosis is an abnormal response of the liver to persistent injury with the excessive accumulation of collagenous extracellular matrices. Liver fibrosis is stimulated by chronic inflammation in liver stimulates (Czaja, A J. 2014. World J Gastroenterol 20, 2515-2532). Masson trichrome and Sirius red staining of collagen, a fibrosis marker, showed high levels of collagen fibers surrounding the central vein and portal area, and overt signs of perisinusoidal fibrosis in liver tissue of HFD-32-fed mice, while liver tissues of HFD-32 fed mice treated with the Retro-Tf-D-LP4 peptide showed almost no collagen staining, suggesting that the peptide treatment prevented inflammation and fibrosis (FIG. 19).

Figure 20:
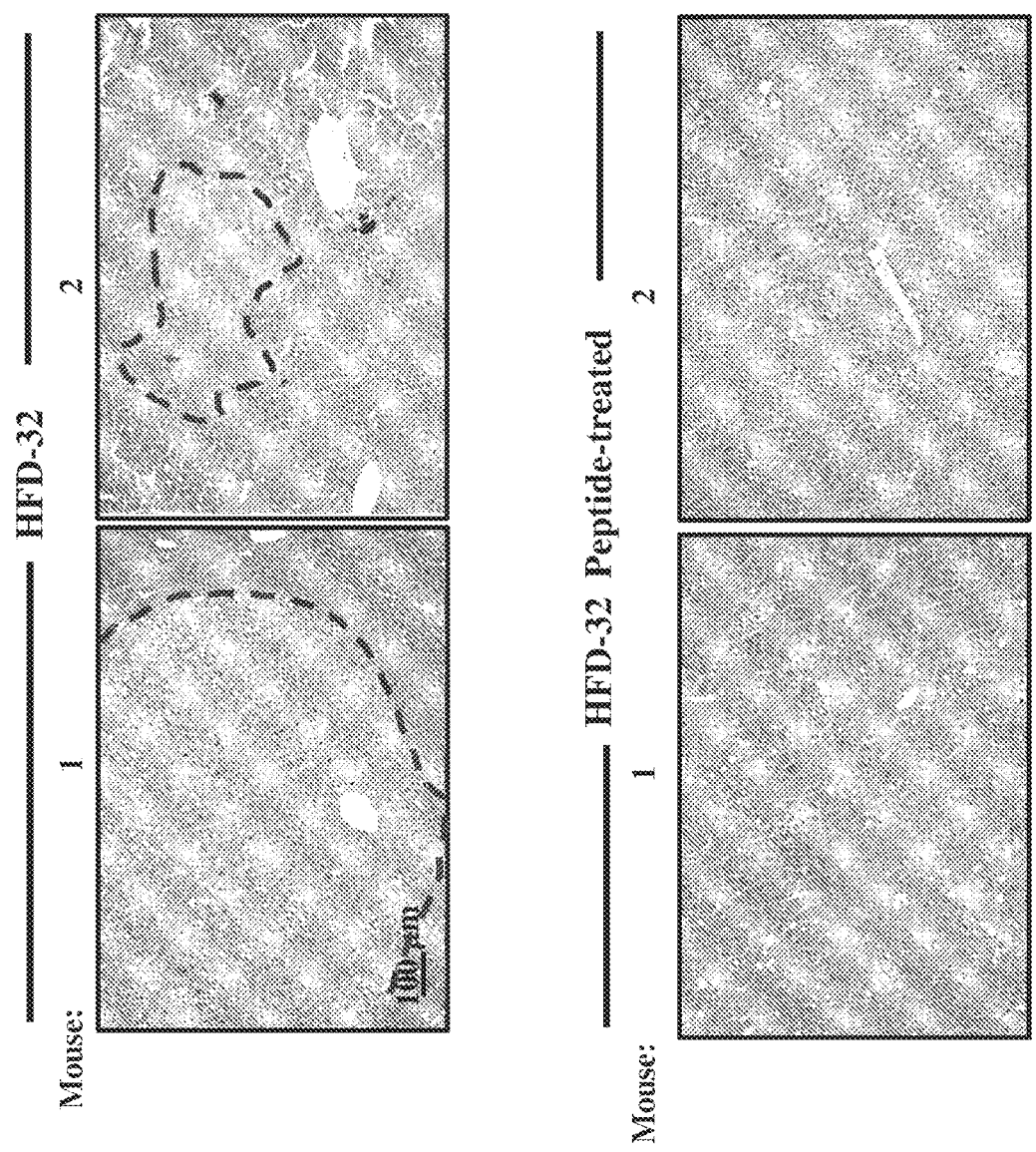
FIG. 20 shows representative H&E staining of liver sections taken from HFD-32-fed mice at week 12 and from Retro-Tf-D-LP4 (10 mg/kg) treated mice. Bar=100 μm. The tumor nodules are labeled by dashed line.

The HFD-32 diet can lead to hepatocellular carcinoma (HCC) (Scorletti E et al. 2014. Hepatology 60, 1211-1221). Therefore, we looked for micro-tumors in mice fed with HFD-32 diet at the NASH stage. Histological sections nodules associated with tumorigenicity are clearly seen (FIG. 20). These nodules were not observed in liver sections of HFD-32-fed mice treated with the peptide, suggesting that the Retro-Tf-D-LP4 peptide also prevented tumor formation.

Tf-D-LP4 Prevents Steatosis and NASH Developed in DEN-Induced HCC

Figure 21A:
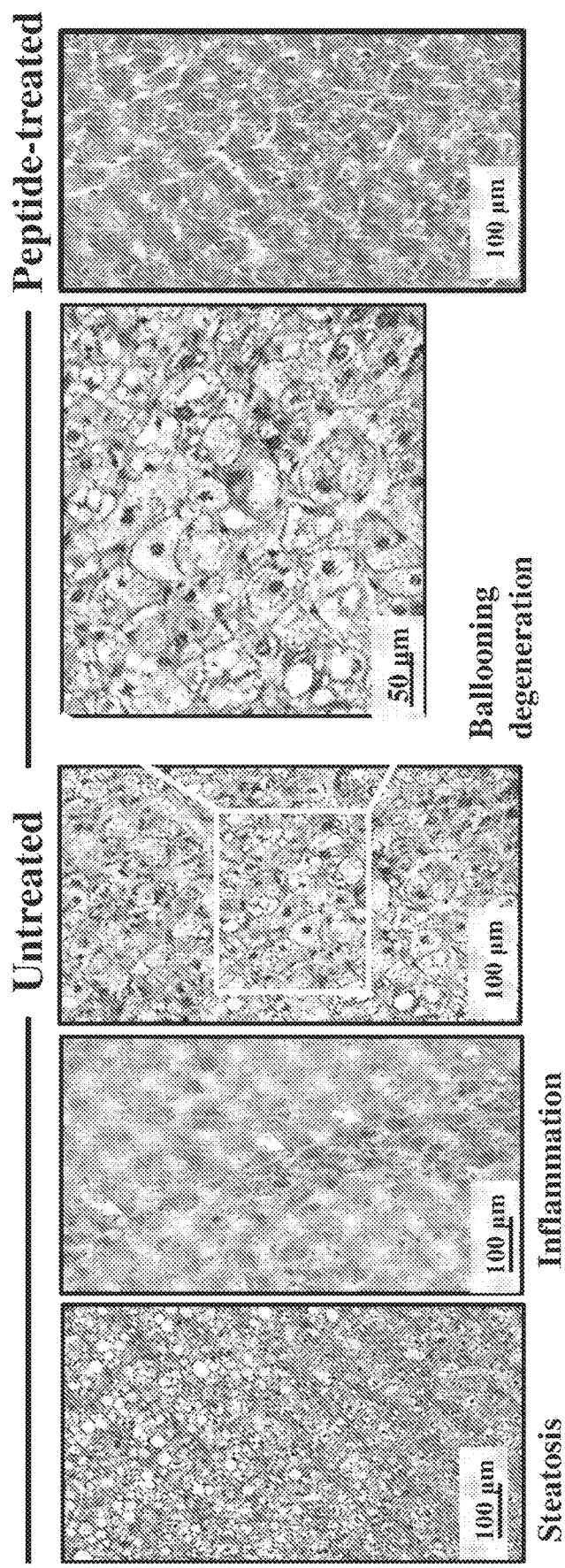
FIG. 21A shows representative H&E staining showing steatosis, inflammation and ballooning in liver sections obtained from mice induced for DEN-induced HCC that did not receive peptide treatment (untreated), but not in Retro-Tf-D-LP4-treated mice (18 mg/Kg i.v.).
Figure 21B:
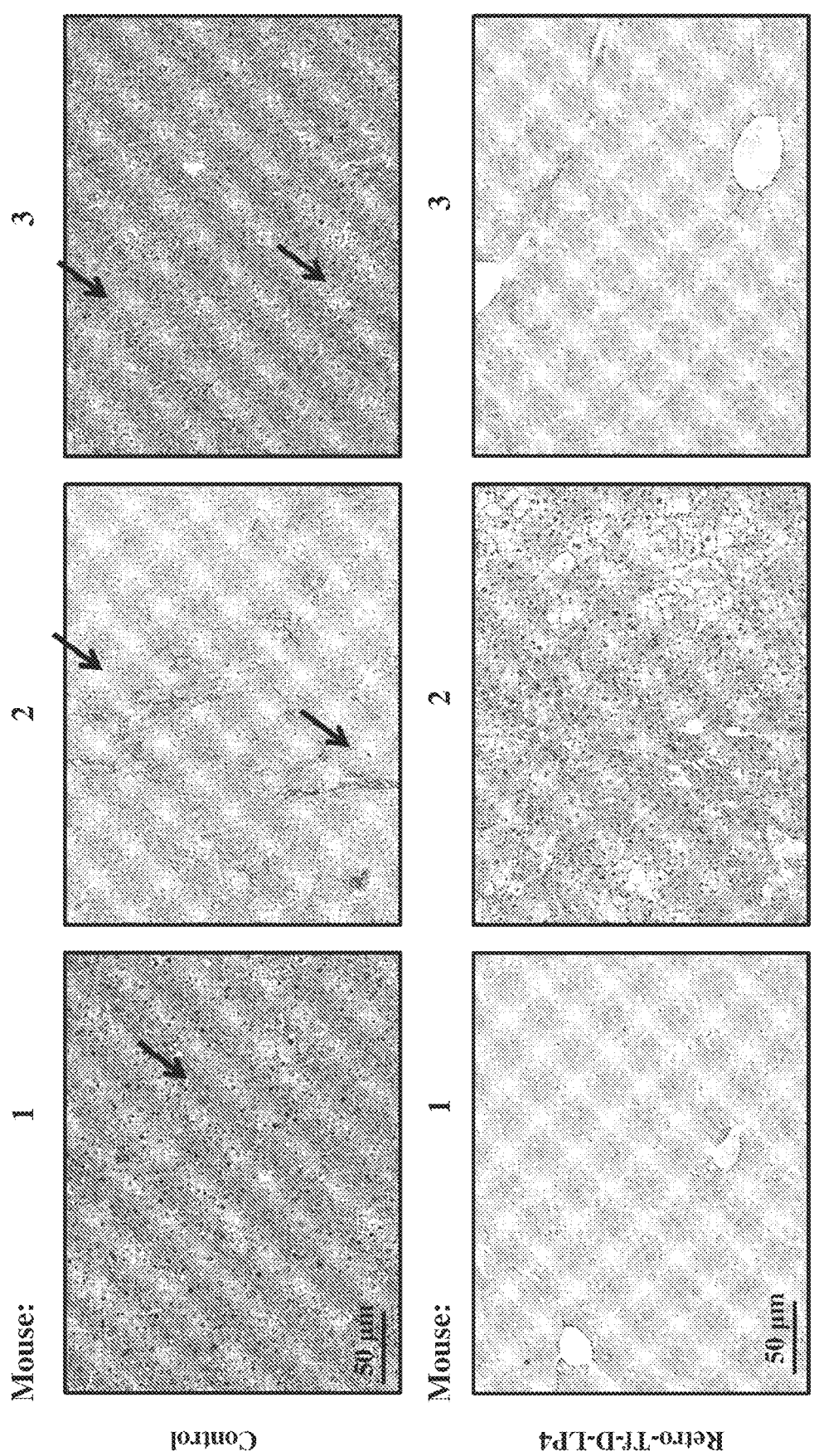
FIG. 21B shows Sirius red staining of liver section from mice induced for cancer by DEN and treated or untreated (control) with the Retro-Tf-D-LP4. Arrows point to the presence of fibrosis

DEN-induced HCC mouse model was produced and treated with the peptide after tumors were visible in livers as described hereinabove. H&E staining of livers from DEN-induced HCC clearly showed that along the tumorigenic process liver pathologies including steatosis, ballooning degradation, inflammation and fibrosis were developed (FIG. 21A, 21B). No such liver pathologies were observed when the mice were treated with the Retro-Tf-D-LP4 peptide (18 mg/Kg) (FIG. 21A, B). These results demonstrate that the peptide prevents HCC development as well as liver associated pathology.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method of treating non-alcoholic fatty liver disease (NAFLD) and/or a symptom associated with NAFLD, the method comprises administering to a subject diagnosed to have NAFLD a therapeutically effective amount of a pharmaceutical composition comprising a synthetic peptide, which comprises (i) an analogue of VDAC1-derived peptide, wherein the analogue comprises the amino acid sequence set forth in SEQ ID NO:2 and is completely inverso modified, and (ii) a recognition and/or localization peptide comprising the amino acid sequence set forth in SEQ ID NO:8, thereby treating the non-alcoholic fatty liver disease (NAFLD) and/or the symptom associated thereto.

2. The method of claim 1, wherein the analogue comprises the amino acid sequence set forth in SEQ ID NO:3.

3. The method of claim 1, wherein the recognition and/or localization peptide is selected from an all L-stereoisomeric peptide and an all D-stereoisomeric peptide.

4. The method of claim 3, wherein the recognition and/or localization peptide is connected to the N- or the C-terminus of the analogue of VDAC1-derived peptide directly or via a linker sequence.

5. The method of claim 4, wherein the synthetic peptide further comprises the amino acid sequence set forth in SEQ ID NO:11 and the amino acid sequence set forth in SEQ ID NO:12, each independently located at the C- or N-terminus of the analogue of VDAC1-derived peptide.

6. The method of claim 4, wherein the synthetic peptide further comprises the amino acid sequence set forth in SEQ ID NO:12 and the amino acid sequence set forth in SEQ ID NO:13, each independently located at the C- or N-terminus of the analogue of VDAC1-derived peptide.

7. The method of claim 6, wherein the synthetic peptide comprises the amino acid sequence set forth in SEQ ID NO:14.

8. The method of claim 1, wherein the NAFLD is selected from the group consisting of non-alcoholic steatosis and non-alcoholic steohepatitis (NASH).

9. The method of claim 1, wherein the symptom associated with NAFLD is selected from the group consisting of fat droplet accumulation, inflammation, fibrosis, hepatocyte cell death and any combination thereof.

* * * * *

SEQUENCE LISTING

```
<160> NUMBER OF SEQ ID NOS: 19

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Lys Lys Leu Glu Thr Ala Val Asn Leu Ala Trp Thr Ala Gly Asn Ser
1               5                   10                  15

Asn

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Asn Ser Asn Gly Ala Thr Trp Ala Leu Asn Val Ala Thr Glu Leu Lys
1               5                   10                  15

Lys

<210> SEQ ID NO 3
<211> LENGTH: 17
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(17)
<223> OTHER INFORMATION: D-amino acid

<400> SEQUENCE: 3

Asn Ser Asn Gly Ala Thr Trp Ala Leu Asn Val Ala Thr Glu Leu Lys
1               5                   10                  15

Lys

<210> SEQ ID NO 4
<211> LENGTH: 26
<212> TYPE: PRT
<213> ORGANISM: Artificial Sequence
<220> FEATURE:
<223> OTHER INFORMATION: Synthetic

<400> SEQUENCE: 4

Met Ala Val Pro Pro Thr Tyr Ala Asp Leu Gly Lys Ser Ala Arg Asp
1               5                   10                  15

Val Phe Thr Lys Gly Tyr Gly Phe Gly Leu
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic

<400> SEQUENCE: 5

Leu Gly Phe Gly Tyr Gly Lys Thr Phe Val Asp Arg Ala Ser Lys Gly
1               5                   10                  15

Leu Asp Ala Tyr Thr Pro Pro Val Ala Met
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(26)
<223> OTHER INFORMATION: D-amino acid

<400> SEQUENCE: 6

Leu Gly Phe Gly Tyr Gly Lys Thr Phe Val Asp Arg Ala Ser Lys Gly
1               5                   10                  15

Leu Asp Ala Tyr Thr Pro Pro Val Ala Met
            20                  25

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

His Ala Ile Tyr Pro Arg His
1               5
```

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

His Arg Pro Tyr Ile Ala His
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic

<400> SEQUENCE: 10

Lys Lys Trp Lys Met Arg Arg Asn Gln Phe Trp Ile Lys Ile Gln Arg
1               5                   10                  15

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Ser Trp Thr Trp Glu
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Lys Trp Thr Trp Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Glu Trp Thr Trp Ser
1               5

<210> SEQ ID NO 14
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(27)
<223> OTHER INFORMATION: D-amino acid

<400> SEQUENCE: 14

Lys Trp Thr Trp Lys Asn Ser Asn Gly Ala Thr Trp Ala Leu Asn Val
1               5                   10                  15

Ala Thr Glu Leu Lys Lys Glu Trp Thr Trp Ser His Arg Pro Tyr Ile
            20                  25                  30

Ala His

<210> SEQ ID NO 15
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(42)
<223> OTHER INFORMATION: D-amino acid

<400> SEQUENCE: 15

Lys Lys Trp Lys Met Arg Arg Asn Gln Phe Trp Ile Lys Ile Gln Arg
1               5                   10                  15

Leu Gly Phe Gly Tyr Gly Lys Thr Phe Val Asp Arg Ala Ser Lys Gly
            20                  25                  30

Leu Asp Ala Tyr Thr Pro Pro Val Ala Met
        35                  40

<210> SEQ ID NO 16
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(42)
<223> OTHER INFORMATION: D-amino acid

<400> SEQUENCE: 16

Arg Gln Ile Lys Ile Trp Phe Gln Asn Arg Arg Met Lys Trp Lys Lys
1               5                   10                  15

Leu Gly Phe Gly Tyr Gly Lys Thr Phe Val Asp Arg Ala Ser Lys Gly
            20                  25                  30

Leu Asp Ala Tyr Thr Pro Pro Val Ala Met
        35                  40

<210> SEQ ID NO 17
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(34)
<223> OTHER INFORMATION: D-amino acid

```
<400> SEQUENCE: 17

His Ala Ile Tyr Pro Arg His Ser Trp Thr Trp Glu Lys Lys Leu Glu
1               5                   10                  15

Thr Ala Val Asn Leu Ala Trp Thr Ala Gly Asn Ser Asn Lys Trp Thr
            20                  25                  30

Trp Lys

<210> SEQ ID NO 18
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(28)
<223> OTHER INFORMATION: D-amino acid

<400> SEQUENCE: 18

Arg Asp Val Phe Thr Lys Gly Tyr Gly Phe Gly Leu Arg Gln Ile Lys
1               5                   10                  15

Ile Trp Phe Gln Asn Arg Arg Met Lys Trp Lys Lys
            20                  25

<210> SEQ ID NO 19
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(22)
<223> OTHER INFORMATION: D-amino acid

<400> SEQUENCE: 19

Lys Trp Thr Trp Lys Asn Ser Asn Gly Ala Thr Trp Ala Leu Asn Val
1               5                   10                  15

Ala Thr Glu Leu Lys Lys Glu Trp Thr Trp Ser His Arg Pro Tyr Ile
            20                  25                  30

Ala His
```